United States Patent [19]

Tsukahara et al.

[11] Patent Number: 5,094,938
[45] Date of Patent: Mar. 10, 1992

[54] SILVER HALIDE COLOR PHOTOGRAPHIC MATERIAL CONTAINING A NOVEL CYAN DYE-FORMING COUPLER

[75] Inventors: Jiro Tsukahara; Shigeru Yamazaki; Hidetoshi Kobayashi, all of Minami-ashigara, Japan

[73] Assignee: Fuji Photo Film Co., Ltd., Kanagawa, Japan

[21] Appl. No.: 598,381

[22] Filed: Oct. 18, 1990

[30] Foreign Application Priority Data

Oct. 18, 1989 [JP] Japan .................. 1-269197
Dec. 18, 1989 [JP] Japan .................. 1-327716
Jun. 21, 1990 [JP] Japan .................. 2-161328

[51] Int. Cl.$^5$ ................................ G03C 7/34
[52] U.S. Cl. ................................ 430/552; 430/553
[58] Field of Search ........................ 430/552, 553

[56] References Cited

U.S. PATENT DOCUMENTS 4,900,656 2/1990 Tani et al. .................. 430/550

FOREIGN PATENT DOCUMENTS

| 0116428 | 8/1984 | European Pat. Off. ........ 430/553 |
| 0271323 | 6/1988 | European Pat. Off. . |
| 59-105644 | 6/1984 | Japan . |
| 59-111643 | 6/1984 | Japan . |
| 59-111644 | 6/1984 | Japan . |
| 0107650 | 6/1985 | Japan .................. 430/553 |
| 1219749 | 9/1989 | Japan .................. 430/553 |

OTHER PUBLICATIONS

Patent Abstracts of Japan, vol. 13, No. 27(P-815)(3375), Jan. 20, 1989 and J-P-A-63-226654.

*Primary Examiner*—Charles L. Bowers, Jr.
*Assistant Examiner*—Lee Wright
*Attorney, Agent, or Firm*—Birch, Stewart, Kolasch & Birch

[57] ABSTRACT

There is disclosed a silver halide color photographic material having a silver halide emulsion layer on a base which comprises a novel cyan coupler. According to the disclosure, a silver halide color photographic material containing a cyan coupler that has high coupling reactivity and high color density, resulting color image being hardly susceptible to reduction fading and is excellent in heat fast can be obtained.

17 Claims, No Drawings

SILVER HALIDE COLOR PHOTOGRAPHIC MATERIAL CONTAINING A NOVEL CYAN DYE-FORMING COUPLER

FIELD OF THE INVENTION

The present invention relates to a silver halide color photographic material containing a novel phenol cyan dye-forming coupler.

BACKGROUND OF THE INVENTION

When a silver halide photographic material is exposed to light and is subjected to color development, dye-forming couplers (hereinafter referred to as couplers) react with the oxidized aromatic primary amine developing agent and color images are formed. Generally, in this method, the color reproduction technique by the subtractive process is used, and in order to reproduce blue, green, and red, color images of yellow, magenta, and cyan complementary to them are formed. In the formation of a cyan color image, phenol derivatives or naphthol derivatives are used as coupler in many cases. In color photography, color-forming couplers are added into a developing solution or are contained in photosensitive photographic emulsion layers or other color-image-forming layers, and the color-forming couplers react with the oxidized product of a color-developing agent formed by the development, thereby forming nondiffusing dyes.

The reaction of a coupler and a color-developing agent takes place at the active site of the coupler, and couplers having a hydrogen atom at that active site are four-equivalent couplers, that is, those couplers that stoichiometrically require four mols of a silver halide having development nuclei to produce 1 mol of a dye. On the other hand, couplers having a coupling releasable group as an anion at the active site are two-equivalent couplers, which stoichiometrically require only two mols of a silver halide having a development nuclei to form 1 mol of a dye. Therefore, in contrast to four-equivalent couplers, two-equivalent couplers generally allow the amount of a silver halide in a photographic layer to be reduced to make the film thinner, the time required for the processing of the photographic material can be made shorter, and further the sharpness of the formed color image is improved.

Of the various cyan couplers, naphthol couplers have hitherto been used widely in photography mainly in color negative films, since the wavelength of the absorption of the produced dye image is sufficiently long, and therefore the absorption less overlaps with the absorption of the magenta dye image, and also the coupling reactivity with the oxidized product of a color developer can be selected to range from a lower one to the higher one. However, since the dye image obtained from naphthol couplers is apt to be reduced with bivalent iron ions built up in an exhausted bleaching solution or bleach-fix solution and to fade (which is referred to as reduction fading), and it is poor in heat fastness, improvement is earnestly desired.

On the other hand, U.S. Pat. No. 4,333,999 discloses phenol cyan couplers having in the 2-position a p-cyanophenylureido group and in the 5-position a carbonamido group that is a ballasting group (diffusion-resistance-providing group). These couplers have come into wide use for said naphthol cyan couplers, since the dye associates in the film, thereby causing a bathchromic shift, which gives a dye image that is excellent in hue and fastness.

However, the performance required for recent photographic materials is severe, and even these couplers are continuously required to have higher coupling reactivity, higher dye absorption density, more excellent color purity, and more excellent fastness of the dye image. To meet these requirements, various studies concerning the 5-position ballasting group have been made and various couplers are disclosed, for example, in JP-A ("JP-A" means unexamined published Japanese patent application) Nos. 105644/1984, 111643/1984, and 111644/1984, U.S. Pat. Nos. 4,753,871, 4,775,616, and 4,849,328, and European Patent Application No. 271,323A. However, even if high coupling reactivity and high dye absorption density were satisfied, the wavelength of the absorption was too short, or even if high dye absorption density and excellent color purity were satisfied, fastness of the dye image was poor, or even if excellent color purity and excellent fastness of the dye image were satisfied, the dye absorption density was low, and therefore it was difficult to satisfy all the requirements.

SUMMARY OF THE INVENTION

Accordingly, the first object of the present invention is to provide a silver halide color photographic material containing a cyan coupler that has high coupling reactivity.

The second object of the present invention is to provide a silver halide color photographic material containing a cyan coupler that gives a high dye absorption density.

The third object of the present invention is to provide a silver halide color photographic material containing a cyan coupler that gives a cyan image excellent in color purity.

The fourth object of the present invention is to provide a silver halide color photographic material containing a cyan coupler that gives a cyan image hardly susceptible to reduction fading during the development processing and that is excellent in heat fastness.

Other and further objects, features and advantages of the invention will appear more evident from the following description.

DESCRIPTION OF THE INVENTION

The inventors have studied keenly to attain the above objects and have found that the objects can be attained by providing the following silver halide color photographic material.

A silver halide color photographic material having at least one silver halide emulsion layer on a base, which silver halide color photographic material comprises at least one cyan dye-forming coupler represented by the following formula (I):

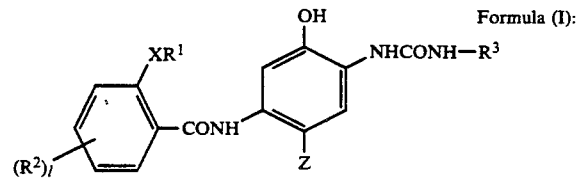

Formula (I):

wherein $R^1$ represents an alkyl group, an alkenyl group, a cycloalkyl group, or an aryl group, $R^2$ represents a group capable of substitution onto a benzene ring, $R^3$ represents an aryl group not containing a condensed ring, X represents —O— or —SO$_2$—, Z represents a hydrogen atom or a group capable of being released upon coupling, and is an integer of 0 to 4.

In the present invention, the groups defined as $R^1$ to $R^3$ include both unsubstituted and substituted ones, as is apparent from specific examples described below.

Some compounds having a p-alkoxybenzamido group as a substituent in the 5-position are described, for example, in JP-A Nos. 204544/1982 (Exemplified Compound No. 21), 201657/1989 (Exemplified Compound No. 26), and 219749/1989 (Exemplified Compound No. 24). Some compounds having a m-alkoxybenzamido group as a substituent in the 5-position are described, for example, in JP-A No. 46644/1984 (Exemplified Compound I-16). Further some compound having an o-alkoxybenzamido group as a substituent in the 5-position are described in JP-A No. 33251/1983 (Exemplified Coupler 5). However, the compounds of the present invention are different from those in that, in the first four cases, the alkoxy group is bonded at positions other than the ortho-position of the benzamido group, and in the last case, an alkoxy group is bonded to the ortho-position, but in the 2-position a heterocycle-substituted ureido group is present instead of an aryl ureido group. Thus, the above objects cannot be attained by these compounds, which will be made clear in Examples below.

Further, some compounds having as a substituent in the 5-position, a p-substituted benzenesulfonylbenzamido group are disclosed, for example, in JP-A Nos. 201657/1989 (Exemplified Compound No. 27) and 19749/1989 (Exemplified Compound No. 25). However they are different from the compounds of the present invention in that a sulfonyl group is bonded to positions other than the ortho-position of the benzamido group. Thus, the above objects cannot be attained by tnese compounds, which will be made clear in the Examples below.

The cyan couplers represented by formula (I) will now be described below in detail.

In Formula (I), $R^1$ represents a straight-chain or branched-chain alkyl group preferably having 1 to 36 (more preferably 6 to 24) carbon atoms (hereinafter referred to as C atoms), a straight-chain or branched-chain alkenyl group having 2 to 36 (more preferably 6 to 24) C atoms, a 3- to 12-membered cycloalkyl group having 3 to 36 (more preferably 6 to 24) C atoms, or an aryl group having 3 to 36 (more preferably 6 to 24) C atoms, which groups may have a substituent (e.g., a halogen atom, a hydroxyl group, a carboxyl group, a sulfo group, a cyano group, a nitro group, an amino group, an alkyl group, an alkenyl group, an alkynyl group, a cycloalkyl group, an aryl group, an alkoxy group, an aryloxy group, an alkylthio group, an alkylsulfonyl group, an arylsulfonyl group, an acyl group, an acyloxy group, an alkoxycarbonyl group, an aryloxycarbonyl group, a carbonamido group, a sulfonamido group, a carbamoyl group, a sulfamoyl group, a ureido group, an alkoxycarbonylamino group, a sulfamoylamino group, an alkoxysulfonyl group, an imido group, and a heterocyclic group, which are hereinafter referred to as substituent group A). Preferably $R^1$ is a straight-chain, branched-chain, or substituted (e.g., alkoxy-, alkylthio-, aryloxy-, arylthio-, alkylsulfonyl-, arylsulfonyl-, aryl-, alkoxycarbonyl-, epoxy-, cyano-, or halogen-substituted) alkyl group [e.g., n-octyl, n-decyl, n-dodecyl, n-hexadecyl, 2-ethylhexyl, 3,5,5-trimethylhexyl, 2-ethyl-4-methylpentyl, 2-hexyldecyl, 2-heptylundecyl, 2-octyldodecyl, 2,4,6-trimethylheptyl, 2,4,6,8-tetramethylnonyl, benzyl, 2-phenetyl, 3-(t-octylphenoxy)propyl, 3-(2,4-di-t-pentylphenoxy)propyl, 2-(4-biphenyloxy)ethyl, 3-dodecyloxypropyl, 2-dodecylthioethyl, 9,10-epoxyoctadecyl, dodecyloxycarbonylmethyl, and 2-(2-naphthyloxy)ethyl], an unsubstituted or substituted (e.g., halogen-, aryl-, alkoxy-, alkylthio-, aryloxy-, arylthio-, or alkoxycarbonyl-substituted) alkenyl group [e.g., ally, 10-undecenyl, oleyl, citronellyl, and cinnamyl], an unsubstituted or substituted (e.g., halogen-, alkyl-, alkoxy-, or aryloxy-substituted) cycloalkyl group [e.g., cyclopentyl, cyclohexyl, 3,5-dimethylcyclohexyl, and 4-t-butylcyclohexyl], or an unsubstituted or substituted (e.g., halogen-, alkyl-, alkoxy-, alkoxycarbonyl-, aryl-, carbonamido-, alkylthio-, or sulfonamido-substituted) aryl group (e.g., phenyl, 4-dodecyloxyphenyl, 4-biphenyl, 4-dodecanesulfonamidophenyl, 4-t-octylphenyl, and 3-pentadecylphenyl], with preference given to the above-mentioned straight-chain, branched-chain, or substituted alkyl groups.

In formula (I), $R^2$ is a group capable of substitution onto a benzene ring and, preferably, a group selected from the above substituent group A, and when l is 2 or over, groups $R^2$ may be the same or different. More preferably $R^2$ is a halogen atom (e.g., F, C , Br, and I), an alkyl group having 1 to 24 C atoms (e.g., methyl, butyl, t-butyl, t-octyl, and 2-dodecyl), a cycloalkyl group having 3 to 24 C atoms (e.g., cyclopentyl and cyclohexyl), an alkoxy group having 1 to 24 C atoms (e.g., methoxy, butoxy, dodecyloxy, benzyloxy, 2-ethylhexyloxy, 3-dodecyloxypropoxy, 2-dodecylthioethoxy, and dodecyloxycarbonylmethoxy), a carbonamido group having 2 to 24 C atoms (e.g., acetamido, 2-ethylhexaneamido, and trifluoroacetamido), or a sulfonamido group having 1 to 24 C atoms (e.g., methanesulfonamido, dodecanesulfonamido, and toluenesulfonamido). Groups $R^2$ may bond together to form a ring.

In formula (I), preferably l is an integer of 0 to 2 and, more preferably, 0 or 1.

In formula (I), $R^3$ is an aryl group not containing a condensed ring and having preferably 6 to 36 and, more preferably, 6 to 15 C atoms, which is preferably a phenyl group, which may be substituted by a group selected from the above substituent group A and may be a condensed ring. As preferable substituents, a halogen atom (F, Cl, Br, and I), a cyano group, a nitro group, an acyl group (e.g., acetyl and benzoyl), an alkyl group (e.g., methyl, t-butyl, trifluoromethyl, and trichloromethyl), an alkoxy group (e.g., methoxy, ethoxy, butoxy, and trifluoromethoxy), an alkylsulfonyl group (e.g., trifluoromethylsulfonyl, propylsulfonyl, butylsulfonyl, and benzylsulfonyl), an arylsulfonyl group (e.g., phenylsulfonyl, p-tolylsulfonyl, and p-chlorophenylsulfonyl), an alkoxycarbonyl group (e.g., methoxycarbonyl and butoxycarbonyl), a sulfonamido group (e.g., methanesulfonamido, trifluoromethanesulfonamido, and toluenesulfonamido), a carbamoyl group (e.g., N,N-dimethylcarbamoyl and N-phenylcarbamoyl), and a sulfamoyl group (e.g., N,N-diethylsulfamoyl and N-phenylsulfamoyl) can be mentioned.

Preferably $R^3$ is a phenyl group having at least one substituent selected among a halogen atom, a cyano group, a sulfonamido group, an alkylsulfonyl group, an arylsulfonyl group, and a trifluoromethyl group and, more preferably, 4-cyanophenyl, 4-cyano-3- halogenophenyl, 3-cyano-4-halogenophenyl, 4-alkylsulfonylphenyl, 4-alkylsulfonyl-3-halogenophenyl, 4-alkylsulfonyl-3-alkoxyphenyl, 3-alkoxy-4-alkylsulfonylphenyl, 3,4-dihalogenophenyl, 4-halogenophenyl, 3,4,5-trihalogenophenyl, 3,4-dicyanophenyl, 3-cyano-4,5-dihalogenophenyl, 4-trifluoromethylphenyl or 3-sulfonamidophenyl, with particular preference given to 4-cyanophenyl, 3-cyano-4-halogenophenyl, 3,4-dicyanophenyl or 4-alkylsulfonylphenyl.

In formula (I), Z represents a hydrogen atom or a group capable of being released upon coupling (including an atom capable of being released, hereinafter the same being applied). As preferable examples of the group capable of being released upon coupling, a halogen atom,

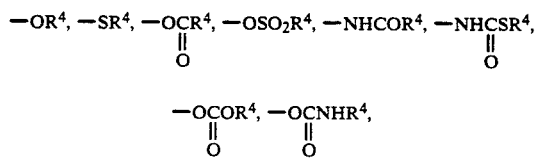

an aryl azo group having 6 to 30 C atoms, and a heterocyclic group having 1 to 30 C atoms and linked to the coupling active site (the position where Z is linked) through the nitrogen atom (e.g., succinimido, phthalimido, hydantoinyl, pyrazolyl, and 2-benztriazolyl) can be mentioned, wherein $R^4$ represents an alkyl group having 1 to 36 C atoms, an alkenyl group having 2 to 36 C atoms, a cycloalkyl group having 3 to 36 C atoms, an aryl group having 6 to 36 C atoms, or a heterocyclic group having 1 to 36 C atoms which may be substituted by a substituent selected among the above-mentioned group A. More preferably Z represents a hydrogen atom, a halogen atom, an alkoxy group, an aryloxy group, or an alkylthio group and, particularly preferably, a hydrogen atom, a chlorine atom, a group represented by formula (II) given below, or a group represented by formula (III) given below:

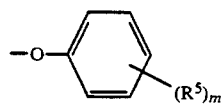

Formula (II)

wherein $R^5$ represents a halogen atom, a cyano group, a nitro group, an alkyl group, an alkoxy group, an alkylthio group, an alkylsulfonyl group, an arylsulfonyl group, a carbonamido group, a sulfonamido group, an alkoxycarbonyl group, a carbamoyl group, a sulfamoyl group, or a carboxyl group, m is an integer of 0 to 5, and when m is 2 or over, groups $R^5$ may be the same or different.

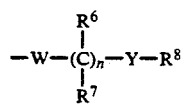

Formula (III)

wherein W represents an oxygen atom or a sulfur atom, $R^6$ and $R^7$ each represent a hydrogen atom or a monovalent group, Y represents

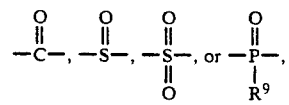

$R^8$ and $R^9$ each represent a hydroxyl group, an alkyl group, an aryl group, an alkoxy group, an alkenyloxy group, an aryloxy group, or a substituted or unsubstituted amino group, n is an integer of 1 to 6, and when n is 2 or over, groups

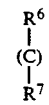

(C) may be the same or different.

In formula (II), $R^5$ preferably represents a halogen atom, an alkyl group (e.g., methyl, t-butyl, t-octyl, and pentadecyl), an alkoxy group (e.g., methoxy, n-butoxy, n-octyloxy, benzyloxy, and methoxyethoxy), an carbonamido group (e.g., acetamido and 3-carboxypropaneamido), or a sulfonamido group (e.g., methanesulfonamido, toluenesulfonamido, and p-dodecyloxybenzenesulfonamido) with particular preference given to an alkyl group or an alkoxy group, and m preferably an integer of 0 to 2 with particular preference given to an integer of 0 to 1.

In formula (III), when $R^6$ and/or $R^7$ each represent a monovalent group, preferably it is an alkyl group (e.g., methyl, ethyl, n-butyl, ethoxycarbonylmethyl, benzyl, n-decyl, and n-dodecyl), an aryl group (e.g., phenyl, 4-chlorophenyl, and 4-methoxyphenyl), an acyl group (e.g., acetyl, decanoyl, benzoyl, and pivaloyl), or a carbamoyl group (e.g., N-ethylcarbamoyl and N-phenylcarbamoyl), and more preferably $R^6$ and $R^7$ each represent a hydrogen atom, an alkyl group, or an aryl group.

In formula (III), W preferably represents an oxygen atom, and Y preferably represents

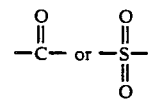

with more preference given to

In formula (III), $R^8$ preferably represents an alkyl group, an alkoxy group, an alkenyloxy group, an aryloxy group, or a substituted or unsubstituted amino group with more preference given to an alkoxy group or a substituted or unsubstituted amino group.

In formula (III), n is preferably an integer of 1 to 3 and, more preferably, 1.

Examples of

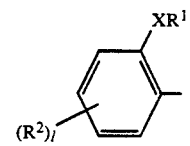

in formula (I) are shown below.
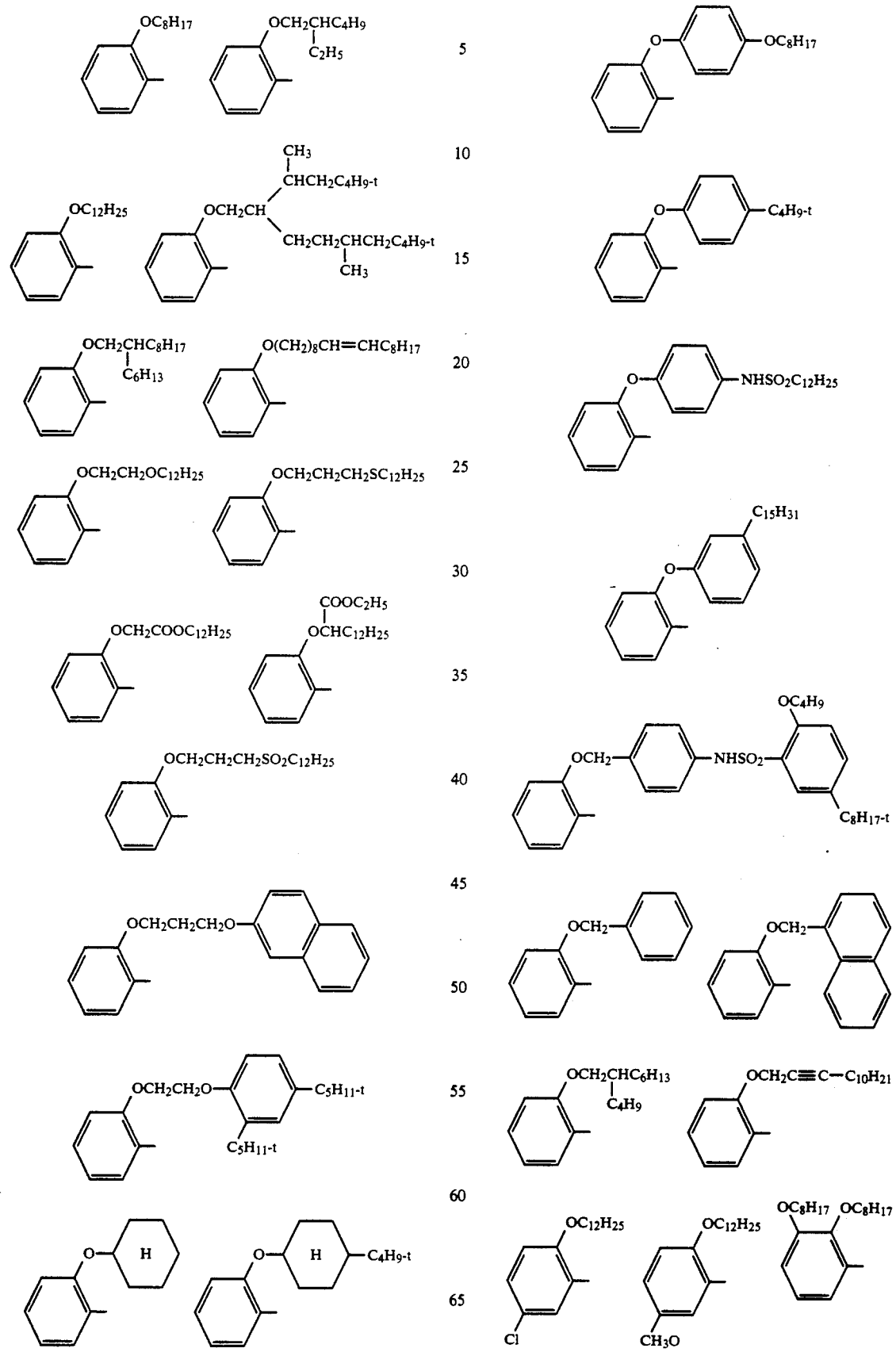

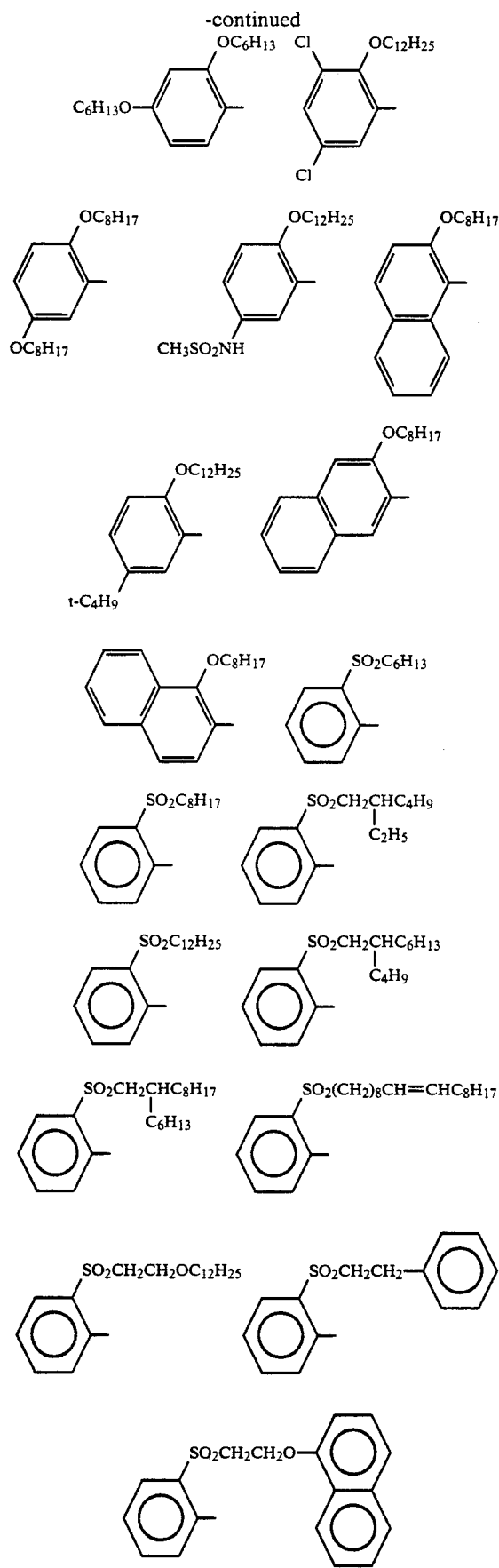
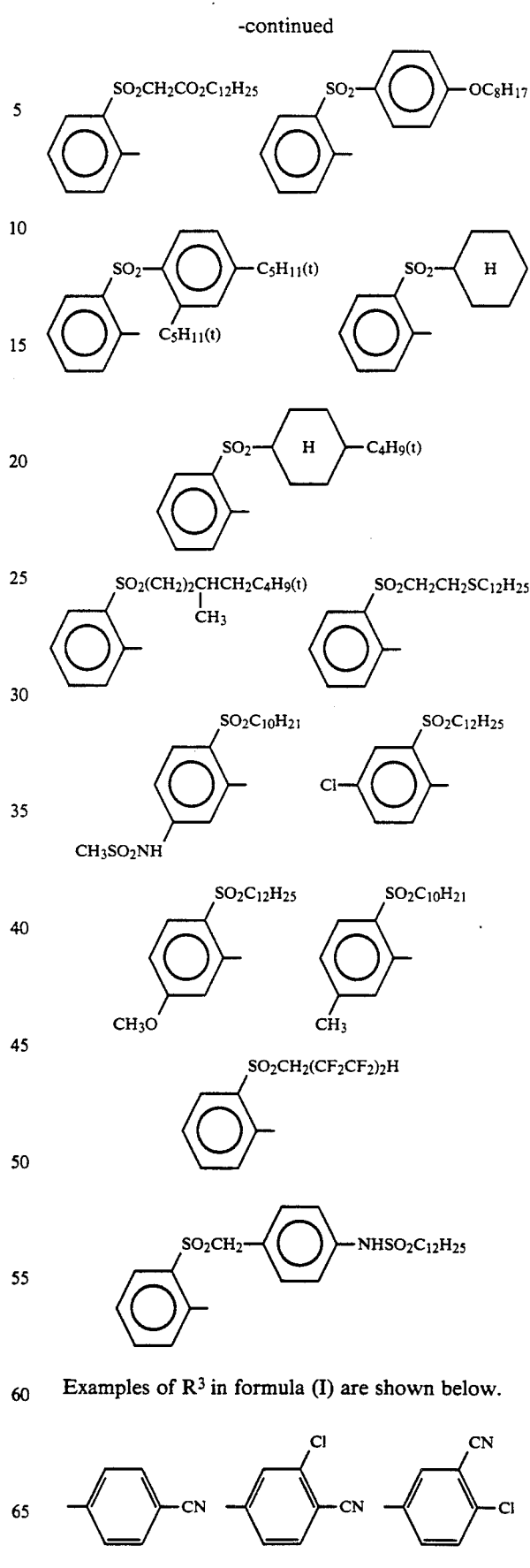
Examples of $R^3$ in formula (I) are shown below.

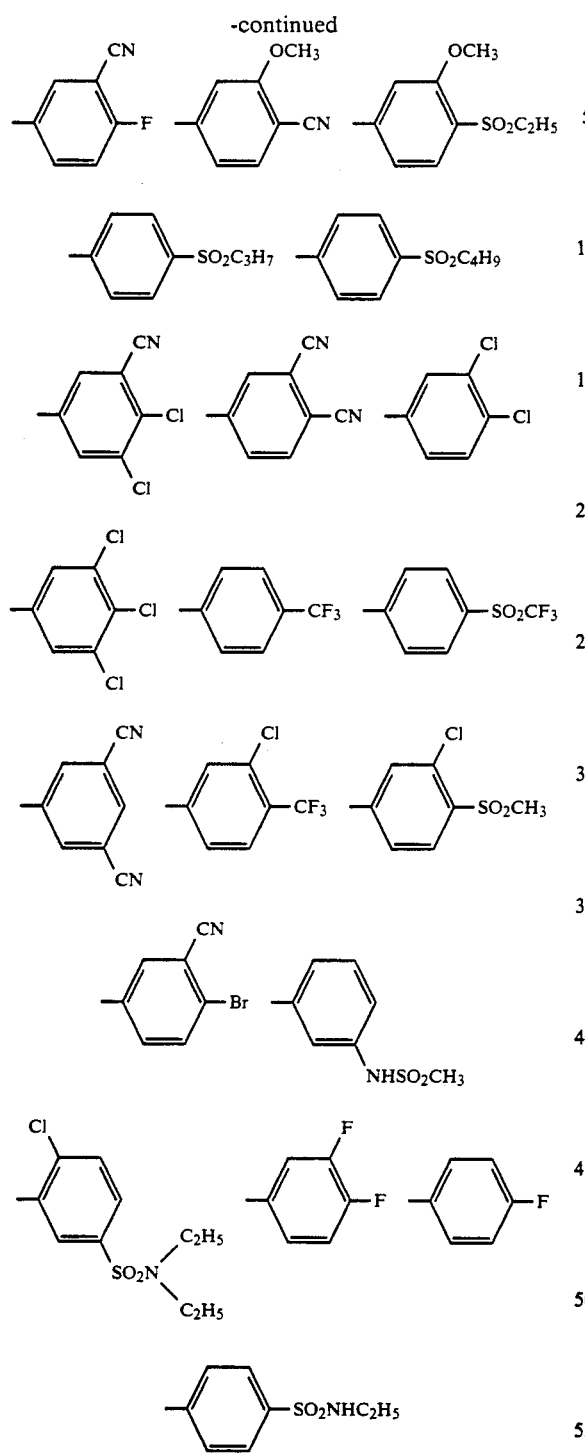
Examples of Z in formula (I) are shown below.
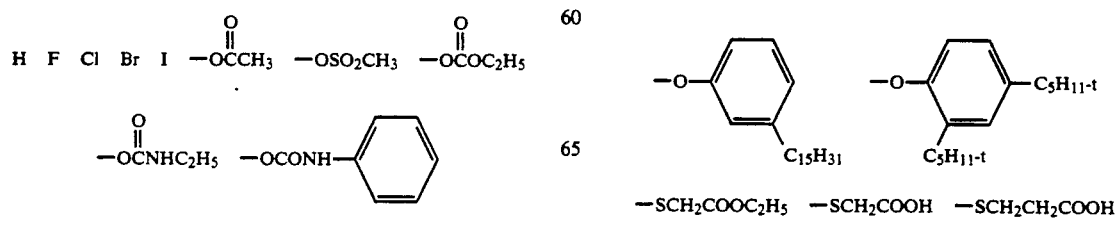
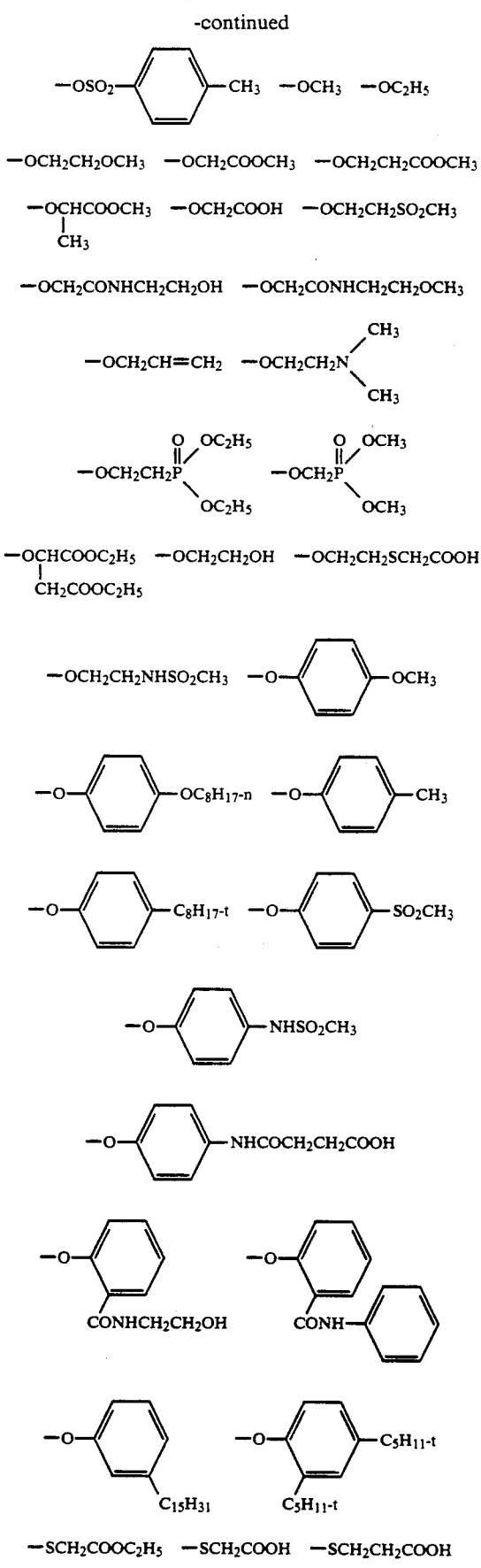

-continued

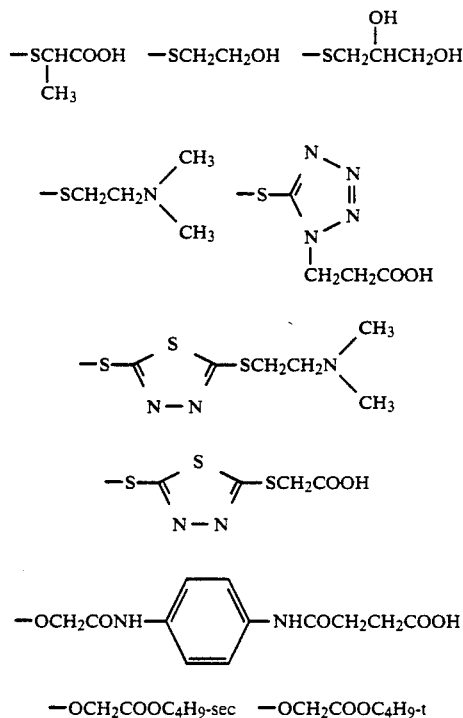
—OCH₂COOC₄H₉-sec   —OCH₂COOC₄H₉-t

-continued

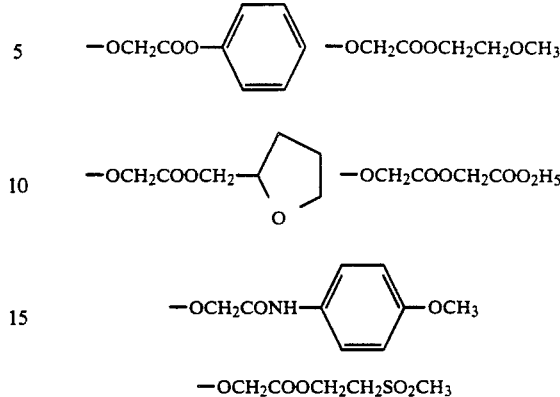

—OCH₂COOCH₂CH₂SO₂CH₃

When Z is a group capable of being released upon coupling, it is preferable that the group does not contain a photographically useful group (e.g., a development-inhibitor residue and a dye residue).

Specific examples of cyan couplers represented by formula (I) are shown below. The number in parentheses is the number of the substitution position of $R^2$.

First, compounds represented by the following formula (Ia) are shown and the synthesis examples thereof are described.

Formula (Ia)

[Structure: 2-OR¹ benzamide with (R²)ₗ substituents at positions 3,4,5,6; CONH linked to phenol ring bearing OH, Z, and NHCONH-R³]

| No. | R¹ | l | R² | R³ | Z |
|---|---|---|---|---|---|
| 1 | $-CH(C_2H_5)CH_2C_4H_9$ | 0 | — | 4-CN-phenyl (with CH₃) | H |
| 2 | $-C_8H_{17}\text{-}n$ | 0 | — | 4-CN-phenyl (with CH₃) | Cl |
| 3 | $-C_{12}H_{25}\text{-}n$ | 0 | — | 4-CN-phenyl (with CH₃) | H |
| 4 | $-CH(CH_3)CH_2CH(CH_3)C_4H_9\text{-}t$ | 0 | — | 2-Cl,4-CN-phenyl (with CH₃) | $-OCH_2COOCH_3$ |
| 5 | $-CH(CH_3)CH_2CH(CH_3)CH_2CHCH_3 (CH_3)$ | 0 | — | 2-CN,4-CH₃-phenyl | $-OCH_2CH_2SO_2CH_3$ |
| 6 | $-CH(C_4H_9)CH_2C_6H_{13}$ | 0 | — | 4-CN-phenyl (with CH₃) | 1,4-dimethoxyphenyl (OCH₃ para OCH₃) |

-continued

Formula (Ia)

[Structure: phenyl ring with OR¹ at position 2, CONH linking to another phenyl ring bearing OH, NHCONH—R³, and Z; (R²)ₗ on first ring]

| No. | R¹ | l | R² | R³ | Z |
|---|---|---|---|---|---|
| 7 | $\underset{\mid}{C_6H_{13}}$<br>—CH₂CHC₈H₁₇ | 0 | — | 4-CN-C₆H₄— | H |
| 8 | $\underset{\mid}{C_7H_9}$<br>—CH₂CHC₉H₁₇ | 0 | — | 4-SO₂C₄H₉-C₆H₄— | —OCHCOOCH₃<br>$\quad\mid$<br>$\quad$CH₃ |
| 9 | $\underset{\mid}{C_8H_{17}}$<br>—CH₂CHC₁₀H₂₁ | 0 | — | 4-CN-C₆H₄— | —O—C₆H₄—C₈H₁₇-t |
| 10 | —C₁₆H₃₃-n | 0 | — | 2-Cl,4-CN-C₆H₃— | —OCHCOOCH₂CH₂NHSO₂C₃H₇<br>$\quad\mid$<br>$\quad$C₄H₉ |
| 11 | —(CH₂)₈CH=CHC₈H₁₇ | 0 | — | 4-CN-C₆H₄— | H |
| 12 | —(CH₂)₂OC₁₂H₂₅-n | 0 | — | 4-CN-C₆H₄— | H |
| 13 | —(CH₂)₃SC₁₂H₂₅-n | 0 | — | 4-CN-C₆H₄— | —OCO-C₆H₅ |

-continued

Formula (Ia)

| No. | R¹ | 1 | R² | R³ | Z |
|---|---|---|---|---|---|
| 14 | $-CH_2COOC_{12}H_{25}\text{-}n$ | 0 | — | 4-CN-phenyl | H |
| 15 | $-CH_2CH_2COOC_{10}H_{21}\text{-}n$ | 0 | — | 4-CF₃-phenyl | H |
| 16 | $\overset{C_{10}H_{21}}{\underset{\phantom{x}}{-CHCOOCH_3}}$ | 0 | — | 2-Cl, 4-CN-phenyl | $-OCH_2COOCH_3$ |
| 17 | $\overset{C_2H_5}{\underset{\phantom{x}}{-CH_2CHC_4H_9}}$ | 0 | — | 2-Cl, 4-CN-phenyl | $-OCH_2CH_2\overset{O}{\underset{\|}{P}}(OC_2H_5)_2$ |
| 18 | $-C_{10}H_{21}\text{-}n$ | 0 | — | 2-OCH₃, 4-SO₂C₂H₅-phenyl | $-OCH_2\overset{O}{\underset{\|}{P}}(OCH_3)_2$ |
| 19 | $-C_{12}H_{25}\text{-}n$ | 0 | — | 2-CN, 4-Cl-phenyl | $-SCH_2CH_2N(CH_3)(CH_2CH_2OCH_3)$ |

-continued

Formula (Ia)

[Structure: phenol derivative with OR¹ at position 2, (R²)ₗ substituent, CONH linking to a second benzene ring bearing OH, NHCONH-R³, and Z]

| No. | R¹ | l | R² | R³ | Z |
|---|---|---|---|---|---|
| 20 | —C₁₁H₂₃-n | 0 | — | 4-(phenylsulfonylmethyl)phenyl (—C₆H₄—SO₂CH₂—C₆H₅) | Cl |
| 21 | —CH₂CH(C₆H₁₃)C₈H₁₇ | 0 | — | 4-CN-C₆H₄— | —OCH₂CH₂SO₂CH₃ |
| 22 | —(CH₂)₃O-(2-naphthyl) | 0 | — | 4-CN-C₆H₄— | H |
| 23 | —(CH₂)₂O-(4-biphenylyl) | 0 | — | 2-F-5-CN-C₆H₃— | H |
| 24 | —C₈H₁₇-n | 1 | —OC₈H₁₇-n (4) | 4-CN-C₆H₄— | H |
| 25 | —C₆H₁₃-n | 1 | —OC₆H₁₃-n (5) | 4-CN-C₆H₄— | H |

-continued

Formula (Ia)

[Structure: benzene ring with OR¹ at position 2, CONH at position 1 connected to another benzene ring with OH, NHCONH—R³, and Z substituents; (R²)ₗ on positions 3,4,5,6]

| No. | R¹ | l | R² | R³ | Z |
|---|---|---|---|---|---|
| 26 | —C₁₂H₂₅-n | 1 | Cl (5) | 4-CN-phenyl | —SCH₂COOCH₃ |
| 27 | —C₁₂H₂₅-n | 1 | —OCH₃ (5) | 4-CN-phenyl | —SCH₂COOH |
| 28 | —C₁₂H₂₅-n | 1 | —NHSO₂CH₃ (5) | 4-CN-phenyl | H |
| 29 | —C₁₀H₂₁-n | 2 | —Cl (3), —Cl (5) | 2-Cl, 5-CN-phenyl | —CH₂COOCH₃ |
| 30 | —CH₂CH(C₆H₁₃)C₈H₁₇ | 1 | —NHSO₂—C₆H₄—OH (5) | 4-CN-phenyl | —SCH₂CH₂N(CH₃)₂ |
| 31 | —CH₂CH(CH₃)CH₂C₄H₉-t | 0 | — | 4-CN-phenyl | H |

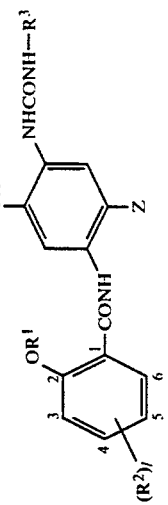

-continued

Formula (Ia)

[Structure: benzene ring with OR¹ at position 2, (R²)ₗ at position 4, CONH at position 1 linking to a second benzene ring bearing OH, NHCONH-R³, and Z substituents]

| No. | R¹ | l | R² | R³ | Z |
|-----|----|----|----|----|----|
| 38 | —(CH₂)₂SC₁₂H₂₅-n | 0 | — | 4-F-C₆H₄ | —OCH₂CONHCH₂CH₂OCH₃ |
| 39 | —C₁₃H₂₇ (branched) | 0 | — | 4-CN-C₆H₄ | H |
| 40 | —C₁₂H₂₅-n | 0 | — | 2,3-Cl₂-6-CN-C₆H₂ | —OCHCOOCH₃<br>      \|<br>      C₂H₅ |
| 41 | —(CH₂)₂OCH₂CHC₄H₉<br>                \|<br>                C₂H₅ | 0 | — | 4-CN-C₆H₄ | H |
| 42 | —(CH₂)₂C₁₀H₂₁-n | 0 | — | 4-CN-C₆H₄ | H |
| 43 | —(CH₂)₃OC₁₂H₂₅ | 2 | (4,5)-cyclohexadiene | 4-CN-C₆H₄ | H |

-continued

Formula (Ia)

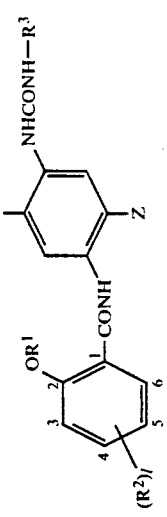

| No. | R¹ | 1 | R² | R³ | Z |
|---|---|---|---|---|---|
| 44 | —(CH$_2$)$_2$OCOC$_{11}$H$_{23}$ | 0 | — |  | H |
| 45 | $\begin{array}{c}C_2H_5\\ —CH_2CHC_4H_9\end{array}$ | 1 | $\begin{array}{c}C_2H_5\\ —OCH_2CHC_4H_9\ (4)\end{array}$ |  | H |
| 46 | $\begin{array}{c}C_2H_5\\ —CH_2CHC_4H_9\end{array}$ | 1 | $\begin{array}{c}C_2H_5\\ —OCH_2CHC_4H_9\ (5)\end{array}$ | 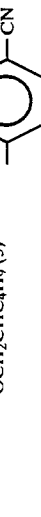 | H |
| 47 | —CH$_3$ | 1 | $\begin{array}{c}C_2H_5\\ —OCH_2CHC_4H_9\ (5)\end{array}$ |  | H |
| 48 | —CH$_3$ | 1 | $\begin{array}{c}C_6H_{13}\\ —OCH_2CHC_8H_{17}\ (5)\end{array}$ |  | H |
| 49 | —CH$_2$— | 1 | $\begin{array}{c}C_2H_5\\ —OCH_2CHC_4H_9\ (5)\end{array}$ |  | H |
| 50 | $\begin{array}{c}C_2H_5\\ —CH_2CHC_4H_9\end{array}$ | 1 | $\begin{array}{c}C_2H_5\\ —OCH_2CHC_4H_9\ (3)\end{array}$ |  | H |

-continued

Formula (Ia):

$$\text{structure with OR}^1\text{ on position 2, (R}^2\text{)}_l\text{ on position 4, CONH linked to a phenol ring bearing OH and NHCONH-R}^3\text{, with Z substituent}$$

| No. | R¹ | l | R² | R³ | Z |
|-----|-----|---|-----|-----|---|
| 51 | —C₁₀H₂₁ (branched) | 0 | — | 4-cyanophenyl | H |
| 52 | —CH₂CHC₈H₁₇ with C₆H₁₃ branch | 0 | — | 4-cyanophenyl | 4-(t-C₈H₁₇)phenoxy |
| 53 | CH₃CHCH₂CHCH₂CH₂CH(CH₂)₃CH₃ with C₂H₅ and CH₃ branches | 0 | — | 4-cyanophenyl | H |
| 54 | C₈H₁₇(n); —CH₂CHC₁₀H₂₁(n) | 0 | — | 4-cyanophenyl | H |
| 55 | C₆H₁₃(n); —CH₂CHC₈H₁₇(n) | 1 | —OCH₂CHC₈H₁₇(n) with C₆H₁₃(n) branch (5) | 4-cyanophenyl | H |
| 56 | C₆H₁₃(n); —CH₂CHC₈H₁₇(n) | 0 | — | 4-cyanophenyl | Cl | wherein —C₁₀H₂₁ (branched) represents a mixed/-branched alkyl group derived from a mixed/branched alcohol having 10 carbon atoms that is obtained by converting propylene trimer to aldehydes by the oxo process followed by reduction, and —C₁₃H₂₇ (branched) represents a mixed/branched alkyl group derived from a mixed/branched alcohol having 13 carbon atoms that is obtained by converting propylene tetramer to aldehydes by the oxo process followed by reduction.

Although the cyan coupler represented by formula (Ia) of the present invention can be synthesized through various synthetic routes, a typical synthetic route is given below.

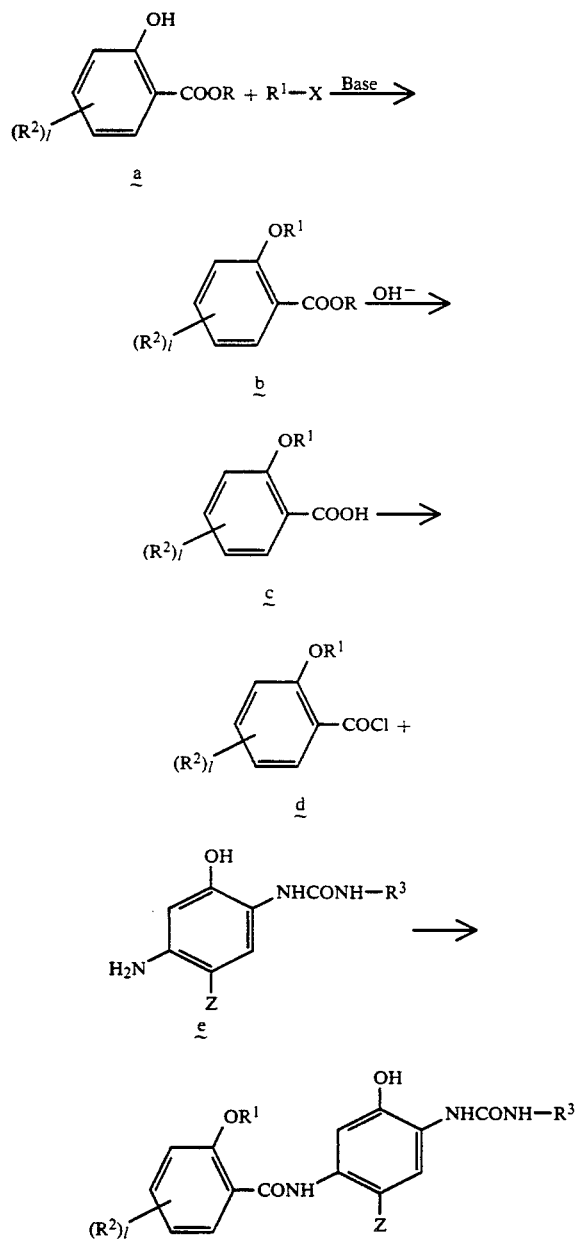

wherein R represents a hydrogen atom, a methyl group, or an ethyl group, X represents a halogen atom, a coupling split-off group such, as a mesyloxy group and a tosyloxy group. The compound b is synthesized by the nucleophilic reaction of a salicylic acid or a salicylate and R¹-X. At that time, it is preferable to use a base such as triethylamine, diazabicycloundecene, sodium carbonate, and a potassium carbonate. The reaction may be carried out without a solvent or it may be carried out using a solvent, such as acetonitrile, N,N-dimethylformamide, N,N-dimethylacetamide, N,N'-dimethylimidazolin-2-on, acetone, and toluene. The reaction temperature is generally −20 to 150° C., more preferably, 20 to 100° C.

If R is an alkyl group, it is led to c. It is general to use an aqueous inorganic base solution, such as an aqueous sodium hydroxide solution, an aqueous potassium hydroxide solution, and an aqueous sodium carbonate solution, and, as a reaction solvent, water or a water-miscible solvent, such as methanol, ethanol, and tetrahydrofuran, is selected. Generally the reaction temperature is −20 to 100° C., preferably 0 to 80° C.

To lead from c to d, thionyl chloride, phosphorus oxychloride, phosphorus pentachloride, oxalyl chloride, etc., are used, and the reaction is carried out without any solvent or in a solvent such as methylene chloride, chloroform, carbon tetrachloride, dichloroethane, toluene, N,N-dimethylformamide, and N,N-dimethylacetamide. The reaction temperature is generally −20 to 150° C., preferably −10 to 80° C.

Compound ~ can be synthesized by the synthesis process described, for example, in U.S. Pat. No. 4,333,999 or JP-A No. 35731/1985, 2757/1986, 42658/1986, or 208562/1988.

The reaction of d with e is carried out without any solvent or in a solvent such as acetonitrile, ethyl acetate, tetrahydrofuran, dioxane, N,N-dimethylformamide, N,N-dimethylacetamide, and N,N'-dimethylimidazolin-2-on at a temperature in the range generally of −20 to 150° C., preferably −10 to 80° C. At that time, a weak base, such as pyridine, imidazole, and N,N-dimethylaniline, may be used. The cyan coupler represented by formula (I) can be synthesized by the direct dehydration condensation of c and e, and wherein as a condensation agent, for example N,N'-dicyclohexylcarbodiimide or carbonyldiimidazole, is used.

Synthesis Examples of couplers of the present invention are described below.

SYNTHESIS EXAMPLE 1

Synthesis of Exemplified Coupler 3

200 ml of N,N-dimethylformamide was added to 18.3 g of ethyl salicylate, and 34.5 g of potassium carbonate and 24.9 g of lauryl bromide were added thereto dropwise over about 30 min with stirring on a steam bath. After the addition the reaction mixture was heated for 2 hours with stirring, then after cooling it was transferred into a separately funnel, and 300 ml of ethyl acetate and 1 l of water were added for extraction. The ethyl acetate solution was washed with dilute hydrochloric acid and then with an aqueous sodium hydrogencarbonate solution and was concentrated, to obtain an oil of 2-dodecyloxybenzoic acid ethyl ester. The oil was dissolved in 300 ml of ethanol, and a solution of 12 g of sodium hydroxide in 50 ml of water was added dropwise thereto over about 10 min at room temperature with stirring. After the addition stirring was continued for 1 hour further and 30 ml of concentrated hydrochloric acid diluted with 300 ml of water was added dropwise. The deposited crystals were filtered, washed with water, and dried to obtain 29.1 g of 2-dodecyloxybenzoic acid.

29.1 g of the dodecyloxybenzoic acid was dissolved in 300 ml of methylene chloride, 1 ml of N,N-dimethylformamide was added, and 24 g of thionyl chloride was added dropwise over about 30 min under heating and reflux. After the addition the heating and refluxing were continued for 2 hours further, and concentration was conducted, to obtain 2-dodecyloxybenzoic acid chloride.

23.1 g of 5-amino-4-chloro-2-[3-(4-cyanophenyl)ureido]phenol synthesized in accordance with the process described in U.S. Pat. No. 4,333,999 was dissolved in 200 ml of N,N-dimethylacetamide, and then the 2-dodecyloxybenzoic acid chloride was added thereto dropwise over 30 min at room temperature under a flow of nitrogen. Thereafter the mixture was stirred for 2 hours and then transferred into a separately funnel. 400 ml of ethyl acetate and 1l of water were added thereto, to effect extraction, and after the ethyl acetate solution was washed with dilute hydrochloric acid and then an aqueous sodium hydrogencarbonate solution, concentration was effected.

500 ml of acetonitrile was added to the concentrate, and after the mixture was heated to dissolve it, crystallization was conducted. The deposited crystals were filtered, washed with acetonitrile, and dried, to obtain 40.3 g of the desired Exemplified Coupler 3. The structure of the coupler was identified by the $^1$H NMR spectrum, mass spectrum, and elemental analysis. The melting point was 171 to 172.5° C.

SYNTHESIS EXAMPLE 2

Synthesis of Exemplified Coupler 7

300 ml of N,N-dimethylacetamide was added to 17.5 g of ethyl salicylate, and 34.6 g of potassium carbonate and then 32.1 of 2-hexyldecyl mesylate were added dropwise over about 30 min with stirring on a steam bath. After the addition the stirring was continued for 2 hours further under heating, and then the reaction mixture was cooled and transferred into a separately funnel. Then 300 ml of ethyl acetate and 1l of water were added for extraction. The ethyl acetate solution was washed with dilute hydrochloric acid, and then with an aqueous sodium hydrogencarbonate solution, and it was concentrated. 300 ml of ethanol was to the coil concentrate, to dissolve the concentrate, and a solution, of 12 g of sodium hydroxide in 50 ml of water was added dropwise thereto over about 10 min at room temperature with stirring. After the addition the stirring was continued for 1 hour further and 30 ml of concentrated hydrochloric acid diluted with 300 ml of water was added dropwise. The reaction liquid was transferred into a separately funnel, and 500 ml of water and 300 ml of ethyl acetate were added for extraction. The ethyl acetate solution was washed with 500 ml of water twice and then concentrated, to obtain 36.0 g of 2-(2-hexyldecyloxy)benzoic acid in the form of an oil.

36.0 g of the 2-(2-hexyldecyloxy)benzoic acid was dissolved in 100 ml of methylene chloride, 0.5 ml of N,N-dimethylformamide was added, and 13 ml of oxalyl chloride was added dropwise over about 30 min at room temperature with stirring. After the addition the stirring was continued for 2 hours further and it was concentrated, to obtain 2-(2-hexyldecyloxy)benzoic acid chloride.

26.8 g of 5-amino-4-chloro-2-[3-(4-cyanophenyl)ureido]phenol was dissolved in 250 ml of N,N-dimethylacetamide, and then the 2-(2-hexyldecyloxy)benzoic acid chloride was added thereto dropwise over 30 min at room temperature under a flow of nitrogen. Thereafter the mixture was stirred for 2 hours and then transferred into a separate funnel. 400 ml of ethyl acetate and 1l of water were added thereto to effect extraction, and after the ethyl acetate solution was washed with dilute hydrochloric acid and then an aqueous sodium hydrogencarbonate solution, concentration was effected. 500 ml of acetonitrile was added to the concentrate, and after the mixture was heated to dissolve it, crystallization was conducted. The deposited crystals were filtered, washed with acetonitrile, and dried, to obtain 48.4 g of the desired Exemplified Coupler 7. The structure of the coupler was identified by the $^1$H NMR spectrum, mass spectrum, and elemental analysis. The melting point was 141.5 to 143° C.

SYNTHESIS EXAMPLE 3

Synthesis of Exemplified Coupler 45

Methyl iodide (20.1 ml, 0.32 mol) was added to a solution of N,N-dimethylformamide (200 ml) containing 2,4-dihydroxybenzoic acid (50.0 g, 0.32 mol) and potassium carbonate (22.4 g, 0.32 mol) at room temperature, and they were stirred for 1 hour. Then water was added, and extraction was effected with ethyl acetate twice. The organic layer was washed with water and then a saturated salt solution and dried over anhydrous sodium sulfate. When the solvent was distilled off under reduced pressure, methyl 2,4-hydroxybenzoate (51.0 g, 94%) was obtained. After 2-ethylhexyl bromide (38.3 g, 0.20 mol) was added dropwise to a DMF solution of the methyl 2,4-hydroxybenzoate (15.4 g, 0.095 mol) and potassium carbonate (40.0 g, 0.29 mol), over 10 min at 60° C., the reaction mixture was stirred for 1 hour. After cooling, water was added and extraction was carried out with ethyl acetate three times. The organic layer was washed with water twice and the solvent was distilled off under reduced pressure, to obtain a coarse product of methyl 2,4-di-(2-ethylhexyloxy)benzoate. A solution of sodium hydroxide (12.0 g, 0.30 mol) in water (30 ml) was added to a solution of the coarse product in ethanol (200 ml) at room temperature and the mixture was stirred for 2 hours. Then water was added thereto and extraction was effected with ethyl acetate three times. The organic layer was washed with 0.1 N hydrochloric acid, water, and then saturated salt water, and it was dried over anhydrous magnesium sulfate. The solvent was distilled off under reduced pressure, and a coarse product (35.2 g) of 2,4-di-(2-ethylhexyloxy)benzoic acid was obtained. N,N-dimethylformamide (1 ml) and oxalyl chloride (15 ml) were added to a solution of the coarse product in methylene chloride (200 ml) and the mixture was stirred for 1 hour. The solvent was distilled off under reduced pressure, to obtain a coarse product of 2,4-dihydroxybenzoic acid chloride.

From this acid chloride and 5-amino-2-[3-(4-cyanophenyl)ureido]phenol (25.9 g, 0.097 mol), Exemplified Coupler 45 (48.3 g, 79 %) was obtained using a procedure similar to the procedure described in Synthesis Example 1. Melting point: 171° C.

SYNTHESIS EXAMPLE 4

Synthesis of Exemplified Coupler 39

Using, as starting materials, ethyl salicylate (16.6 g, 0.10 mol) and 1-mesyloxytridecane (branched) (27.8 g, 0.10 mol), a coarse product (29.4 g) of tridecyloxybenzoic acid chloride was obtained in a manner similar to that in Synthesis Example 1, and it was reacted with 5-amino-2-(4-cyanophenylureido)phenol (23.4 g, 0.087 mol), to obtain Exemplified Coupler 39 (38.2 g, 77%).

SYNTHESIS EXAMPLE 5

Synthesis of Exemplified Coupler 53

Using, as starting materials, ethyl salicylate (16.6 g, 0.10 mol) and 7-ethyl-4-mesyloxy-2-methylundecane (29.2 g, 0.10 mol), 2-(1-isobutyl-4-ethyl)octyloxybenzoic acid chloride was obtained in a manner similar to that in Synthesis Example 1, and it was reacted with 5-amino-2-[3-(4-cyanophenyl)ureido]phenol (26.8 g, 0.10 mol), to obtain Exemplified Coupler 53 (47.3 g, 81%). Melting point: 128° C.

SYNTHESIS EXAMPLE 6

Synthesis of Exemplified Coupler 54

Using, as starting materials, ethyl salicylate (16.7 g, 0.10 mol) and 1-mesyloxy-2-octyldodecane (37.6 g, 0.01 mol), 2-(2-octyl)dodecyloxybenzoic acid chloride was obtained in a manner similar to that in Synthesis Example 1, and it was reacted with 5-amino-2-[3-(4-cyanophenyl)ureido]phenol (26.8 g, 0.10 mol), to obtain Exemplified Coupler (48.3 g, 72%). Melting point: 133° C.

SYNTHESIS EXAMPLE 7

Synthesis of Exemplified Coupler 55

Using a procedure similar to that in Synthesis Example 3, Exemplified Coupler 55 (49.2 g, 68 %) was obtained from 2,5-dihydroxybenzoic acid (15.2 g, 0.10 mol), 2-hexyl-1-mesyloxydecane (64.2 g, 0.20 mol), and 5-amino-2-[3-(4-cyanophenyl)ureido]phenol (22.8 g, 0.085 mol). Melting point: 94° C.

SYNTHESIS EXAMPLE 8

Synthesis of Exemplified Coupler 52

From 2-(2-hexyldecyloxy)benzoic acid chloride (30.4 g, 0.08 mol), synthesized using the procedure described in Synthesis Example 2, and 5-amino-2-[3-(4-cyanophenyl)ureido]-4-(t-octylphenoxy)phenol (39.0 g, 0.08 mol), synthesized by the method described in U.S. Pat. specification No. 4,333,999, Exemplified Coupler 52 (60.6 g, 91%) was obtained by a procedure similar to that in Synthesis Example 2. Melting point: 170° C.

SYNTHESIS EXAMPLE 9

Synthesis of Exemplified Coupler 56

From 2-(2-hexyldecyloxy)benzoic acid chloride (30.4 g, 0.08 mol), synthesized by the procedure stated in Synthesis Example 2, and 5-amino-4-chloro-2-[3-(4-cyanophenyl)ureido]phenol (24.2 g, 0.08 mol), synthesized by the method described in U.S. Pat. specification No. 4,333,999, Exemplified Coupler 56 (45.5 g, 88%) was obtained by a procedure similar to that in Synthesis Example 2. Melting point: 194° C.

The structures of Exemplified Couplers 45, 39, 53, 54, 55, 52, and 56 were identified by each $^1$H NMR spectrum, mass spectrum, and elemental analysis.

The mesyloxy compounds used in Synthesis Examples 4 to 7 can be produced easily by letting a methylene chloride solution of the corresponding alcohol interact with methanesulfonyl chloride in the presence of a base, such as triethylamine.

Examples of cyan couplers represented by the following formula (Ib) are shown below:

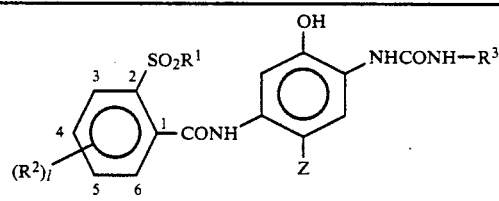

(Ib)

| No. | $R^1$ | 1 | $R^2$ | $R^3$ | Z |
|---|---|---|---|---|---|
| 101 | —$C_{10}H_{21}$(n) | 0 | — | ![4-cyano-2-fluorophenyl] | H |
| 102 | —$CH_2CHC_4H_9$(n) <br> \| <br> $C_2H_5$ | 0 | — | ![4-cyanophenyl] | H |
| 103 | —$CH_2CHC_4H_9$(n) <br> \| <br> $C_2H_5$ | 0 | — | ![4-chloro-3-cyanophenyl] | H |
| 104 | —$CH_2CH_2CHCH_2C_4H_9$(t) <br> \| <br> $CH_3$ | 0 | — | ![4-cyanophenyl] | H |
| 105 | —$C_{12}H_{25}$(n) | 0 | — | ![4-cyanophenyl] | H |
| 106 | —$CH_2CHC_6H_{13}$(n) <br> \| <br> $C_4H_9$(n) | 0 | — | ![4-butylsulfonylphenyl] | Cl |

-continued

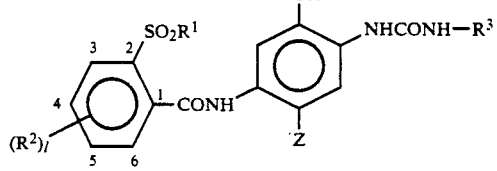

(Ib)

| No. | R¹ | l | R² | R³ | Z |
|---|---|---|---|---|---|
| 107 | $-CH_2CHC_8H_{17}(n)$ with $C_6H_{13}(n)$ | 0 | — | 4-CN-phenyl | H |
| 108 | $-CH_2CHCH_3CH_2C_4H_9(t)$ with $CH_2CH_2C_4H_9(t)$, $CH_3$ branches | 0 | — | 4-CN-phenyl | $-OCO$-phenyl |
| 109 | $-CH_2CH_2OC_{12}H_{25}(n)$ | 0 | — | 4-CN-phenyl | H |
| 110 | $-(CH_2)_8CH=CHC_8H_{17}(n)$ | 0 | — | 3,4-di-CN-phenyl | $-OCH_2COOCH_3$ |
| 111 | $-CH$ with $CH_2CH(CH_3)_2$, $C_2H_5$, $CH_2CH_2CHC_4H_9(n)$ | 0 | — | 3,4-di-Cl-phenyl | Cl |
| 112 | $-CH_2CH_2OCH$ with $CH_2CH(CH_3)_2$, $C_2H_5$, $CH_2CH_2CHC_4H_9(n)$ | 0 | — | 3-CN-4-F-phenyl | $-OCH_2CH_2SO_2CH_3$ |
| 113 | $-CH_2CH_2O$-biphenyl | 0 | — | 4-CN-phenyl | H |
| 114 | $-CH_2COOC_{12}H_{25}(n)$ | 0 | — | 4-CN-phenyl | $-OCH_2COOH$ |
| 115 | $-CH_2CH_2$-phenyl | 0 | — | 4-CN-phenyl | H |
| 116 | $-CH_2$-cyclohexyl | 0 | — | 3-NHSO$_2$CH$_3$-phenyl | H |
| 117 | cyclohexyl-$C_8H_{17}(t)$ | 0 | — | 3-Cl-4-CN-phenyl | $-OCH_2COOCH_3$ |
| 118 | $-C_{18}H_{37}(n)$ | 0 | — | 3-COOC$_2$H$_5$-phenyl | $-OCHCOOC_2H_5$ with $CH_3$ |
| 119 | $-CH_2CH_2CHCH_2C_4H_9(t)$ with $CH_3$ | 0 | — | 4-CN-phenyl | $-OCH_2CH_2P(O)(OC_2H_5)_2$ |
| 120 | $-C_{16}H_{33}(n)$ | 0 | — | 4-CN-phenyl | $-O$-phenyl-$NHCOCH_2CH_2COOH$ |

-continued

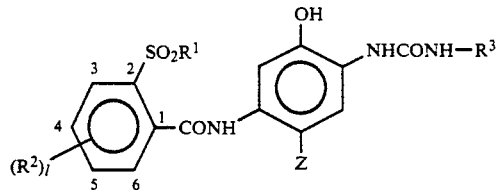
(Ib)

| No. | R¹ | l | R² | R³ | Z |
|---|---|---|---|---|---|
| 121 | —CH₂CH(C₂H₅)C₄H₉(n) | 0 | — | 4-CN-C₆H₄— | —O—C₆H₄—OCH₃ |
| 122 | —C₁₂H₂₅(n) | 0 | — | 4-CN-C₆H₄— | —O—C₆H₄—C₈H₁₇(t) |
| 123 | —CH₂CH(C₆H₁₃(n))C₈H₁₇(n) | 0 | — | 4-CN-C₆H₄— | —SCH₂COOH |
| 124 | —C₁₀H₂₁(n) | 0 | — | 2-Cl-4-CN-C₆H₃— | —SCH₂CH₂N(CH₃)₂ |
| 125 | —CH₂CH(C₆H₁₃(n))C₈H₁₇(n) | 1 | Cl(4) | 2-CN-4-Cl-C₆H₃— | —O—C₆H₄—C₈H₁₇ |
| 126 | —C₁₄H₂₉(n) | 1 | —NHSO₂CH₃(4) | 4-CN-C₆H₄— | Cl |
| 127 | —C₁₂H₂₅(n) | 1 | Cl(5) | 3,4-Cl₂-5-CN-C₆H₂— | Cl |
| 128 | 3,5-(C₅H₁₁(t))₂-C₆H₃— | 1 | —OCH₃(4) | 2-OCH₃-4-SO₂C₂H₅-C₆H₃— | Cl |
| 129 | —C₁₀H₂₁(n) | 1 | —OCH₃(4), —OCH₃(5) | 4-CN-C₆H₄— | —OCH₂CONHCH₂CH₂OCH₃ |
| 130 | 2-(OCH₂CH(C₆H₁₃(n))C₈H₁₇(n))-C₆H₄— | 0 | — | 4-CN-C₆H₄— | Cl |
| 131 | 4-C₁₂H₂₅-C₆H₄— | 0 | — | 2-CN-4-Cl-C₆H₃— | —SCH₂CH₂N(CH₃)(CH₂CH₂CO₂CH₃) |
| 132 | 2-(NHSO₂C₁₀H₂₁(n))-C₆H₄— | 0 | — | 4-CN-C₆H₄— | H |
| 133 | 2-(SO₂C₁₂H₂₅(n))-C₆H₄— | 0 | — | 4-CN-C₆H₄— | H |

-continued
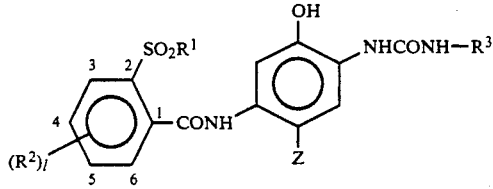
(Ib)
| No. | R¹ | l | R² | R³ | Z |
|---|---|---|---|---|---|
| 134 | —⌬—COOC₈H₁₇(n) | 0 | — | ⌬ with CN, F | H |
| 135 | ⌬—SCH₂CH(C₂H₅)C₄H₉(n) | 0 | — | ⌬ with Cl, CN | Cl |
| 136 | ⌬—⌬ | 0 | — | ⌬—CN | H |
| 137 | ⌬—OC₈H₁₇(t) | 0 | — | ⌬—NHSO₂CH₃ | —OCH₂COOCH₃ |
| 138 | ⌬ with OC₆H₁₃, OC₆H₁₃ | 0 | — | ⌬—COOC₂H₅ | —O—⌬—OCH₃ |
| 139 | ⌬ with OCH₂CH(CH₃)C₂H₅, OCH₂CH(CH₃)C₂H₅ | 0 | — | ⌬ with Cl, Cl, CN | —O—⌬—OCH₃ |
| 140 | ⌬—NHCOC₄H₉(t) | 1 | —Cl(4) | ⌬ with F, CN | —O—⌬—OCH₃ |
| 141 | ⌬—OCH₂CH(CH₃)CH₃ | 1 | —Cl(5) | ⌬—CN | —SCH₂CH₂COOH |
| 142 | ⌬ with OCH₃, CO—⌬ | 1 | —OCH₃(4) | ⌬—CN | —SCH₂CH₂OH |
| 143 | ⌬—⌬(H) | 1 | —OCH₃(3), —OCH₃(5) | ⌬—CN | Cl |
| 144 | ⌬—⌬ | 0 | — | ⌬—CN | H |

-continued

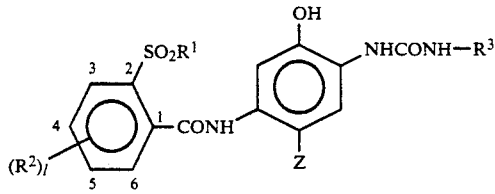
(Ib)

| No. | R¹ | l | R² | R³ | Z |
|---|---|---|---|---|---|
| 145 | ![structure with C₈H₁₇(t) and CN] | 0 | — | —⟨⟩—CN | Cl |
| 146 | $-CH_2CHCH_2C_4H_9(t)$ with CH₃ branch and $CH_2CH_2CHCH_2C_4H_9(t)$ with CH₃ branch | 0 | — | —⟨⟩—CN | H |
| 147 | $CH_2CH(CH_3)_2$ / $-CH$ / $CH_2CH_2CHC_4H_9(n)$ with $C_2H_5$ | 0 | — | —⟨⟩—CN | H |

Although the cyan coupler represented by formula (Ib) of the present invention can be synthesized through various synthetic routes, a typical synthetic route is given below.

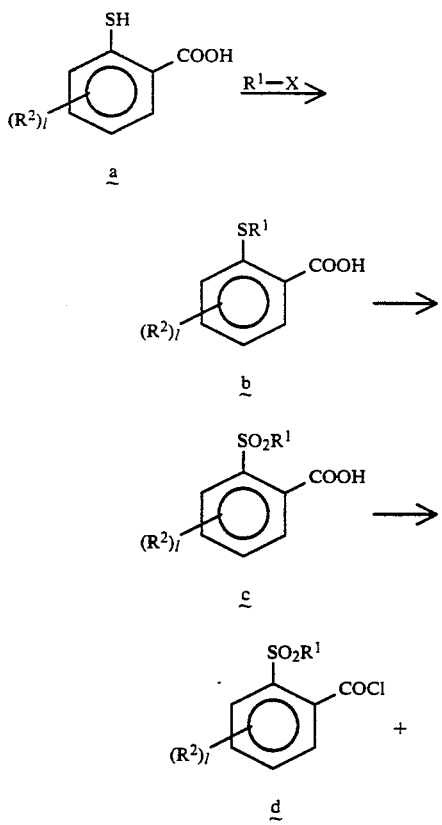

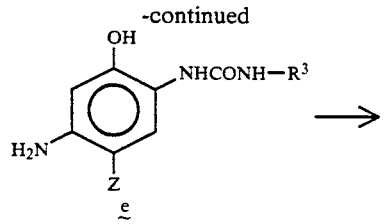

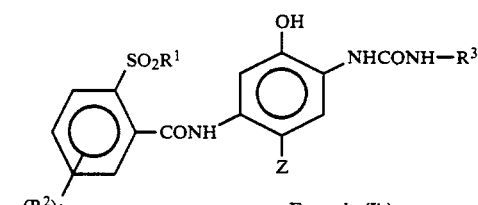

Formula (Ib)

Compound b can be synthesized by reacting a thiosalicylic acid with an alkyl halide or a substituted alcohol. A reaction solvent may or may not be used. As the reaction solvent, ethyl acetate, acetonitrile, toluene, tetrahydrofuran, dioxane, N,N-dimethylformamide, N,N-dimethylacetamide, methylene chloride, or chloroform can be used. In this reaction, a base may be used. As the base, potassium carbonate, sodium carbonate, sodium hydroxide, potassium hydroxide, pyridine, p-dimethylaminopyridine, DABCO (diazabicyclooctane), triethylamine, N-methylmorpholine, DBU (diazabicyloundecene), and DNB (diazabicyclononene) can be mentioned. The reaction temperature is −50 to 200° C., preferably 0 to 150° C.

To lead from b to c, hydrogen peroxide, sodium metaperiodide, m-chloroperbenzoic acid, monoperoxyphthalic acid magnesium salt hexahydrate, performic acid, peracetic acid, trifluoroperacetic acid, a permanganate, chromic acid, ruthenium tetroxide, ozone, anodization, hydrogen peroxide/sodium tungstate, or the like is used. As the solvent, acetic acid, methylene chloride, chloroform, carbon tetrachloride, methanol, ethanol, isopropanol, t-butanol, or the like is used. Generally the reaction temperature is −30 to 200° C., preferably −30 to 80° C.

To lead from $\underline{c}$ to $\underline{d}$, thionyl chloride, phosphorus oxychloride, phosphorus pentachloride, oxalyl chloride, etc., are used, and the reaction is carried out without any solvent or in a solvent such as methylene chloride, chloroform, carbon tetrachloride, dichloroethane, toluene, N,N-dimethylformamide, and N,N-dimethylacetamide. The reaction temperature is generally −20 to 150° C., preferably −10 to 80° C.

Compound $\underline{e}$ can be synthesized by the synthesis process described, for example, in U.S. Pat. No. 4,333,999, or JP-A No. 35731/1985, 2757/1986, 42658/1986, or 208562/1988.

The reaction of $\underline{d}$ with $\underline{e}$ is carried out without any solvent or in a solvent such as acetonitrile, ethyl acetate, tetrahydrofuran, dioxane, N,N-dimethylformamide, N,N-dimethylacetamide, and N,N'-dimethylimidazolin-2-on at a temperature in the range generally of −20 to 150° C., preferably −10 to 80° C. At that time, a weak base, such as pyridine, imidazole, and N,N-dimethylaniline, may be used. The cyan coupler represented by formula (I) can be synthesized by the direct dehydration condensation of $\underline{c}$ and $\underline{e}$, wherein as a condensation agent, for example N,N'-dicyclohexylcarbodiimide or carbonyldiimidazole, is used.

SYNTHESIS EXAMPLE 10

Synthesis of Exemplified Compound 105

Potassium carbonate (20.0 g, 0.145 mol) was added to a solution of thiosalicylic acid (15.4 g, 0.10 mol) and lauryl bromide (24.9 g, 0.10 mol) in DMF (200 ml) and the mixture was stirred at 90° C. for 2 hours. After cooling, the reaction mixture was stirred into 1 l of 1 N hydrochloric acid and the deposited crystals were filtered.

The crystals were dissolved in acetic acid and then 0.7 g of sodium tungstate was added to the solution. Hydrogen peroxide (0.12 equivalent) was added thereto at room temperature, and the reaction mixture was stirred at 70° C. for 2 hours. After cooling, an aqueous sodium sulfite solution was added thereto and then extraction was carried out with ethyl acetate. The organic layer was washed with 0.1 N hydrochloric acid, then water, and then a saturated salt water, and then it was dried over anhydrous magnesium sulfate. The solvent was distilled off under reduced pressure and the concentrate was recrystallized from acetonitrile, to obtain o-dodecanesulfonylbenzoic acid (31.1 g, 81%).

The o-dodecanesulfonylbenzoic acid (30.0 g, 0.084 mol) was dissolved in 100 ml of methylene chloride, then 0.5 ml of N,N-dimethylformamide was added, and they were stirred at room temperature. Then 12 ml of oxalyl chloride was added dropwise over 15 min, and after the addition the reaction mixture was stirred for 1 hour. The reaction solution was concentrated, to obtain o-dodecanesulfonylbenzoyl chloride.

The o-dodecanesulfonylbenzoyl chloride was added dropwise at 60° C. to a solution of 5-amino-2-[3-(4-cyanophenyl)ureido]phenol (synthesized in accordance with the synthesis process described in U.S. Pat. specification No. 4,333,999) in N,N-dimethylacetamide (200 ml) under a flow of nitrogen, and they were stirred well.

After cooling, water was added and extraction was carried out with ethyl acetate twice. The organic layer was washed with 0.1 N hydrochloric acid twice, with water once, and with a saturated salt water once, and it was dried over anhydrous sodium sulfate. The solvent was distilled off under reduced pressure and the residue was recrystallized from acetonitrile, to obtain Exemplified Compound 105 (40.4 g, 79%).

SYNTHESIS EXAMPLE 11

Synthesis of Exemplified Compound 107

Using a procedure similar to that in Synthesis Example 10, Exemplified Compound 107 (46.4 g, 74%) was obtained from thiosalicylic acid (15.4 g, 0.10 mol), 2-hexyl-1-mesyloxydecane (32.0 g, 0.10 mol), and 5-amino-2-[3-(4-cyanophenyl)ureido]phenol (25.5 g, 0.095 mol). Melting point: 115° C.

SYNTHESIS EXAMPLE 12

Synthesis of Exemplified Compound 146

Using a procedure similar to that in Synthesis Example 10, Exemplified Compound 146 (45.1 g, 69%) was obtained from thiosalicylic acid (15.4 g, 0.10 mol), 2,2,4,8,10,10-hexamethyl-6-mesyloxymethylundecane (34.8 g, 0.10 mol), and 5-amino-2-[3-(4-cyanophenyl)ureido]phenol (25.5 g, 0.095 mol). Melting point: 184° C.

SYNTHESIS EXAMPLE 13

Synthesis of Exemplified Compound 147

Using a procedure similar to that in Synthesis Example 1, Exemplified Compound 147 (42.6 g, 71%) was obtained from thiosalycylic acid (15.4 g, 0.10 mol), 7-ethyl-2-methyl-4-mesyloxyundecane (29.2 g, 0.10 mol), and 5-amino-2-[3-(4-cyanophenyl)ureido]phenol (25.5 g, 0.095 mol). Melting point: 174° C.

Mesylates of alcohols used in Synthesis Examples 11, 12, and 13 can easily be synthesized from the corresponding alcohols. That is, a solution of the corresponding alcohol in methylene chloride is interacted with methanesulfonyl chloride in the presence of a base, such as triethylamine, at 0° C.

In the present invention, said cyan coupler is used generally in an amount of 0.002 to 2 mol, more preferably 0.01 to 1 mol, per mol of the photosensitive silver halide. The coating amount per square meter is 0.01 to 5 millimol, preferably 0.1 to 2 millimol.

The cyan coupler of the present invention can be introduced into a photographic material by the oil-in-water dispersion process. A high-boiling organic solvent can be used in a weight ratio of from 2.0 to 0, preferably from 1.0 to 0, and more preferably 0.1 to 0 to the coupler, which is smaller than that of other cyan couplers having similar structures and allows stable dispersion. The feature of the present invention is that a stable dispersion can be obtained without using a high-boiling organic solvent.

In the present invention, although, as a coupler solvent, ones given below can be used, for the cyan coupler it is preferable to use a high-boiling organic solvent, such as a phthalate (e.g., dibutyl phthalate, di-2-ethylhexyl phthalate, didodecyl phthalate, and ethylphthalylethyl glycolate), a fatty acid ester (e.g., 2-ethylhexyl tetradecanoate, di-2-ethylhexyl adipate, di-2-ethylhexyl sebacate, and 2-ethylhexyl-9,10-epoxy stearate), a benzoate (e.g., 2-ethylhexyl benzoate, dodecyl benzoate, and hexadecyl-4-hydroxy benzoate), a phenol (e.g., 2,4-di-t-pentylphenol, 2,4-dinonylphenol, and 2,4-didodecyl phenol), or a chlorinated paraffin (e.g., a paraffin having a chlorine content of 40 to 70 wt. %).

It is preferable to use a high-boiling organic solvent having a relative dielectric constant of about 6.5 or below, more preferably 6.5 to 5, measured at 25° C. and 10 Hz. Phthalates of long-chain alkyl alcohols that have a relative dielectric constant of about 5.2 are preferable, because the obtained color shade has a long wavelength.

Although the cyan coupler of the present invention can be used in any of a photosensitive emulsion layer, a non-photosensitive emulsion layer, and an intermediate layer, the cyan coupler is preferably used to be added to a photosensitive emulsion layer, and more preferably a red-sensitive emulsion layer.

The cyan coupler of the present invention can be used alone or in combination with other cyan coupler is. As the cyan couplers that can preferably be used in combination with the present cyan couplers, 1-naphthol cyan couplers, 5-amido-1-naphthol cyan couplers (described in U.S. Pat. Nos. 690899 and JP-A No. 78252/1989), and 2-ureido phenol cyan couplers (JP-A No. 2044/1989) can be mentioned.

The coupler of the present invention can be adopted to, for example, a color paper, a color reverse paper, a color positive film, a color negative film, a color reverse film, or a color direct positive photographic material, with particular preference given to a color negative film.

The silver halide emulsion of the color photographic material to be used in the present invention may be any type of halogen composition, including silver bromide, silver iodobromide, silver bromochloroiodide, silver chlorobromide or silver chloride.

Although the halogen compositions of the emulsion may be the same or different from grain to grain, if emulsions whose grains have the same halogen composition are used, it is easy to make the properties of the grains homogeneous. With respect to the halogen composition distribution in a silver halide emulsion grain, for example, a grain having a so-called uniform-type structure, wherein the composition is uniform throughout the silver halide grain, a grain having a so-called layered-type structure, wherein the halogen composition of the core of the silver halide grain is different from that of the shell (which may comprise a single layer or layers) surrounding the core, or a grain having a structure with nonlayered parts different in halogen composition in the grain or on the surface of the grain (if the nonlayered parts are present on the surface of the grain, the structure has parts different in halogen composition joined onto the edges, the corners, or the planes of the grain) may be suitably selected and used. To secure high sensitivity, it is more advantageous to use either of the latter two than to use grains having a uniform-type structure, which is also preferable in view of the pressure resistance. If the silver halide grains have the above-mentioned structure, the boundary section between parts different in halogen composition may be a clear boundary, or an unclear boundary, due to the formation of mixed crystals caused by the difference in composition, or it may have positively varied continuous structures.

The composition of silver halide may be changed according to the purpose of the photographic material to be adopted. For example, a silver halide emulsion comprising mainly silver chlorobromide may be used for a print material, such as a color paper, while an emulsion comprising mainly silver iodobromide being used for a photographic material, such as a color negative film.

Further in the photographic material suitable for a rapid processing an emulsion of high silver chloride content, so-called a high-silver-chloride emulsion may be preferably used. The content of silver chloride of the high-silver-chloride emulsion is preferably 90 mol % or over, more preferably 95 mol % or over.

In these high-silver-chloride emulsions, the structure is preferably such that the silver bromide localized layer in the layered form or nonlayered form is present in the silver halide grain and/or on the surface of the silver halide grain as mentioned above. The silver bromide content of the composition of the above-mentioned localized layer is preferably at least 10 mol %, and more preferably over 20 mol %. The localized layer may be present in the grain, or on the edges, or corners of the grain surfaces, or on the planes of the grains, and a preferable example is a localized layer epitaxially grown on each corner of the grain.

The average grain size of the silver halide grains (expressed in terms of the grain diameter for spherical or semi-spherical grains, the edge length for cubic grains, and the spherical diameter for tabular grains, which can be determined as the average of the projected area diameter) is preferably smaller than 2 μm and larger than 0.1 μm, most preferably smaller than 1.5 μm and larger than 0.15 μm. The distribution of grain size may be either narrow or wide, but it is preferable in the present invention to use the so-called monodisperse emulsion of silver halide having a value (deviation coefficient) obtained by dividing the standard deviation calculated from the size distribution curve by the average grain size of 20% or less, most preferably 15% or less. In order to realize the gradation desired for the photographic material, two or more monodisperse silver halide emulsions (preferably all emulsions having the above-mentioned deviation coefficient) different in grain size may be mixed in a single layer or coated as different layers that have substantially the same color sensitivity. Further, two or more polydisperse silver halide emulsions or a combination of monodisperse and polydisperse emulsions can be used.

Silver halide grains for use in the present invention may have a regular crystal structure, such as cubic, hexahedral, rhombic dodecahedral, tetradecahedral, or a mixture thereof, or an irregular crystal structure, such as spherical or thereof composite crystal structure. Further tabular grains can be employed.

The silver halide photographic emulsions that can be used in this invention may be prepared suitably by known means, for example, by the methods described in *I. Emulsion Preparation and Types*, in *Research Disclosure* (RD), No. 17643 (December 1978), pp. 22-23, and in ibid, No. 18716 (November 1979), p. 648; the methods described in P. Glafkides, *Chemie et Phisicue Photographicue*, Paul Montel (1967), in G.F. Duffin, *Photographic Emulsion Chemistry*, Focal Press (1966), and in V. L. Zelikman et al., *Making and Coating of Photographic Emulsion*, Focal Press (1964).

A monodisperse emulsion, such as described in U.S. Pat. Nos. 3,574,628 and 3,655,394, and in British Pat. No. 1,413,748, is also preferable.

Tabular grains having an aspect ratio of 5 or greater can be used in the emulsion of this invention. Tabular grains can be easily prepared by the methods described in, for example, Gutoof, *Photographic Science and Engineering*. Vo. 14, pp. 248-257 (1970), U.S. Pat. Nos.

4,434,226, 4,414,310, 4,433,048, and 4,439,520, and British Pat. No. 2,112,157.

The crystal structure of the emulsion grains may be uniform, the outer halogen composition of the crystal structure may be different from the inner halogen composition, or the crystal structure may be layered. Silver halides whose compositions are different may be joined by the epitaxial joint, or a silver halide may be joined, for example, to a compound other than silver halides, such as silver rhodanide, lead oxide, etc.

Further, the silver halide may be a mixture of grains having various crystal shapes.

The silver halide emulsion may generally be physically ripened, chemically ripened, and spectrally sensitized. Additives that will be used in these steps are described in *Research Disclosure* No. 1763 and ibid. No. 18716, and involved sections are listed in the Table shown below.

Known photographic additives that can be used in this invention are also described in the above-mentioned two Research Disclosure, and the involved sections are listed in the same Table below.

| Additive | RD 17643 | RD 18716 |
| --- | --- | --- |
| 1 Chemical sensitizer | p. 23 | p. 648 (right column) |
| 2 Sensitivity-enhancing agents | — | p. 648 (right column) |
| 3 Spectral sensitizers and Supersensitizers | pp. 23–24 | pp. 648 (right column) –649 (right column) |
| 4 Brightening agents | p. 24 | — |
| 5 Antifogging agents | pp. 24–25 | p. 649 (right column) |
| 6 Light absorbers, Filter dyes, and UV Absorbers | pp. 25–26 | pp. 649 (right column) –650 (left column) |
| 7 Stain-preventing agents | p. 25 (right column) | p. 650 (left to right column) |
| 8 Image-dye stabilizers | p. 25 | — |
| 9 Hardeners | p. 26 | p. 651 (left column) |
| 10 Binders | p. 26 | p. 651 (left column) |
| 11 Plasticizers and Lubricants | p. 27 | p. 650 (right column) |
| 12 Coating aids and Surface-active agents | pp. 26–27 | p. 650 (right column) |
| 13 Antistatic agents | p. 27 | p. 650 (right column) |

Further, in order to prevent the lowering of photographic performances due to folmaldehyde gas, a compound described in, for example, U.S. Pat. Nos. 4,411,987 and 4,435,503 that is able to react with formaldehyde to immobilize it can be added to the photographic material.

Various color couplers can be used in this invention, and typical examples are described in the patents in the above-mentioned *Research Disclosure* No. 17643, VII-C to G.

As yellow couplers, those described, for example, in U.S. Pat. Nos. 3,933,501, 4,022,620, 4,326,024, 4,401,752, and 4,428,961, JP-B ("JP-B" means examined Japanese Pat. publication) No. 10739/1983, British Pat. Nos. 1,425,020 and 1,476,760, U.S. Pat. Nos. 3,973,968, 4,314,023, and 4,511,649, and European Pat. No. 249,473A are preferable.

As magenta couplers, the 5-pyrazolone type and pyrazoloazole type are preferable, and those described in U.S. Pat. Nos. 4,310,619 and 4,315,897, European Pat. No. 73,636, U.S. Pat. Nos. 3,061,432 and 3,725,067, *Research Disclosure* No. 24220 (June 1984), JP-A No. 33552/1985, *Research Disclosure* No. 24230 (June 1984), JP-A Nos. 43659/1985, 72238/1986, 35730/1985, 118034/1980, and 185951/1985, U.S. Pat. Nos. 4,500,630, 4,540,654, and 4,556,630, and International Patent Publication No. WO 88/04795 are particularly preferable.

The cyan couplers that can be used in combination with the compound of this invention include phenol-type couplers and naphthol-type couplers, and those described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011, and 4,327,173, West German Pat. Application (OLS) No. 3,329,729, European Pat. Nos. 121,365A and 249,453A, U.S. Pat. Nos. 3,446,622, 4,333,999, 4,775,616, 4,451,559, 4,427,767, 4,690,889, 4,254,212, and 4,296,199, and JP-A No. 42658/1986 are more preferable.

As a colored coupler to rectify the unnecessary absorption of color-forming dyes, those couplers described in paragraph VII-G of *Research Disclosure* No. 17643, U.S. Pat. No. 4,163,670, JP-B No. 39413/1982, U.S. Pat. Nos. 4,004,929 and 4,138,258, British Pat. No. 1,146,368 are preferable. Further, it is preferable to use couplers to rectify the unnecessary absorption of color-forming dye by fluorescent dye released upon the coupling described in U.S. Pat. No. 4,774,181 and couplers having a dye precursor, as a group capable of being released, that can react with the developing agent to form a dye described in U.S. Pat. No. 4,777,120.

As a coupler which forms a dye having moderate diffusibility, those described in U.S. Pat. No. 4,366,237, British Pat. No. 2,125,570, European Pat. No. 96,570, West German Pat. Application (OLS) No. 3,234,533 are preferable.

Typical examples of a polymerized dye-forming coupler are described in U.S. Pat. Nos. 3,451,820, 4,080,211, 4,367,282, 4,409,320, and 4,576,910, and British Pat. No. 2,102,173.

A coupler that releases a photographically useful residue accompanied with the coupling reaction can be used favorably in this invention. As a DIR coupler that releases a development retarder, those described in patents cited in paragraph VII-F of the above-mentioned *Research Disclosure* No. 17643, JP-A Nos. 151944/1982, 54234/1982, 184248/1985, 37346/1988, and 37350/1988, and U.S. Pat. Nos. 4,286,962 and 4,782,012 are preferable.

As a coupler which releases, imagewisely, a nucleating agent or a development accelerator upon developing, those described in British Pat. Nos. 2,097,140 and 2,131,188, and JP-A Nos. 157638/1984 and 70840/1984 are preferable.

Other couplers that can be incorporated in the photographic material of this invention include competitive couplers described in U.S. Pat. No. 4,130,427, multi-equivalent couplers described in U.S. Pat. Nos. 4,283,472, 4,338,393, and 4,310,618, couplers which release a DIR redox compound, couplers which release a DIR coupler, and redox compounds which release a DIR coupler or a DIR redox described in JP-A Nos. 185950/1985 and 24252/1987, couplers which release a dye to regain a color after releasing described in European Pat. Nos. 173,302A and 313,308A, couplers which release a bleaching-accelerator described in RD. Nos. 11449 and 24241, and JP A No. 201247/1986, couplers which release a ligand described in U.S. Pat. No. 4,553,477, couplers which release a leuco dye described in JP-A No. 75747/1988, and couplers which release a fluorescent dye described in U.S. Pat. No. 4,774,181.

The couplers to be used in this invention can be incorporated to photographic materials by various known dispersing processes.

Examples of a high-boiling organic solvent for use in the oil-in-water dispersing process are described, for example, in U.S. Pat. No. 2,332,027.

The steps and effects of the latex dispersion method and examples of latex for impregnation are described, for example, in U.S. Pat. No. 4,199,363, and West German Pat. Application (OLS) Nos. 2,541,274 and 2,541,230, and a dispersion method using a polymer soluble in an organic solvent is described in PCT International Publication No. WO 88/00723.

Specific examples of high-boiling organic solvents that are used in the above-mentioned oil-in-water dispersing process include alkylester phthalate (e.g., dibutyl phthalate and dioctyl phthalate), phosphate ester (e.g., diphenyl phosphate, triphenyl phosphate, tricresyl phosphate, and dioctylbutyl phosphate), citrate ester (e.g., tributylacetyl citrate), benzoate ester (e.g., 2-ethylhexyl benzoate and 2-ethylhexyl-2,4-dichloro benzoate), alkylamide (e.g., diethyllaurylamide), ester of aliphatic acid (e.g., dibutoxyethyl succinate, di-2-ethylhexyl succinate, 2-hexyldecyl tetradecanate, tributyl citrate, and dietyl azelate), chlorinated paraffin (paraffin having a chlorine content of 10 to 80%), and ester of trimethinate (e.g., tributyl trimethinate), or organic solvents having a boiling point of about 30 to 150° C., for example, lower alkyl acetate such as ethyl acetate and butyl acetate, ethyl propionate, secondary butyl alcohol, metylisobutyl ketone, β-ethoxyethyl acetate and methyl cellosolve acetate may be used in combination.

The amount of color coupler to be able to use in combination is, as a standard, in a range of 0.001 to 1 mol per mol of silver halide, preferably 0.1 to 0.5 mol for yellow coupler, 0.003 to 0.3 mol for magenta coupler, and 0.002 to 0.3 mol for cyan coupler, per mol of silver halide.

In the color photographic material of this invention, it is preferable to add various preservatives or mildew proofing agents, such as 1,2-benzisothiazoline-3-one, n-butyl-p-hydroxy benzoate, phenol, 4-chloro-3,5-dimethyl phenol, 2-phenoxyethanol, and 2-(4-thiazolyl)-benzimidazole, as described in JP-A Nos. 257747/1988, 72248/1987, and 80941/1989.

The photographic material of this invention is prepared by coating on a flexible base, such as plastic film (e.g., cellulose nitrate, cellulose acetate, and polyethylene terephthalate) and paper, as usually used, and on a rigid base, such as glass plate. Details of the base and coating method are described in *Research disclosure*, Vol. 176, Item 17643, paragraph XV (p. 27) and paragraph XVIII (p. 28)(December 1978).

The photographic material that is prepared by using this invention may contain, as color antifoggant, for example, a hydroquinone derivative, an aminophenol derivative, a gallic acid derivative, or an ascorbic acid derivative.

In the photographic material of the present invention, various anti-fading agent (discoloration preventing agent) can be used. That is, as organic anti-fading additives for cyan, magenta and/or yellow images, hydroquinones, 6-hydroxychromans, 6-hydroxycoumarans, spirochromans, hindered phenols including p-alkoxyphenols and bisphenols, gallic acid derivatives, methylenedioxybenzenes, aminophenols, hindered amines, and ether or ester derivatives obtained by silylating or alkylating the phenolic hydroxyl group of these compounds can be mentioned typically. Metal complexes such as (bissalicyl-aldoximato) nickel complex and (bis-N,N-dialkyldithiocarbamato) nickel complex can also be used.

Specific examples of the organic anti-fading agents are described in the following patent specifications:

Hydroquinones are described, for example, in U.S. Pat. Nos. 2,360,290, 2,418,613, 2,700,453, 2,701,197, 2,728,659, 2,732,300, 2,735,765, 3,982,944, and 4,430,425, British Pat. No. 1,363,921, and U.S. Pat. Nos. 2,710,801 and 2,816,028; 6-hydroxychromans, 5-hydroxycoumarans and spirochromans are described, for example, in U.S. Pat. Nos. 3,432,300, 3,573,050, 3,574,627, 3,698,909, and 3,764,337, and JP-A No. 152225/1977; spiroindanes are described in U.S. Pat. No. 4,360,589; p-alkoxyphenols are described, for example, in U.S. Pat. No. 2,735,765, British Pat. No. 2,066,975, JP-A No. 10539/1984, and JP-B No. 19765/1982; hindered phenols are described, for example, in U.S. Pat. No. 3,700,455, JP-A No. 72224/1977, U.S. Pat. No. 4,228,235, and JP-B No. 623/1977; gallic acid derivatives, methylenedioxybenzenes, and aminophenols are described, for example, in U.S. Pat. Nos. 3,457,079 and 4,332,886, and JP-B No. 21144/1981 respectively; hindered amines are described, for example, in U.S. Pat. Nos. 3,336,135 and 4,286,593, British Pat. Nos. 1,326,889, 1,354,313, and 1,410,846, JP-B No. 1420/1976, and JP-A Nos. 114036/1983, 53846/1984, and 78344/1984, and metal complexes are described, for example, in U.S. Pat. Nos. 4,050,938 and 4,241,155 and British Pat. No. 2,027,731(A). To attain the purpose, these compounds can be added to the photosensitive layers by coemulsifying them with the corresponding couplers, with the amount of each compound being generally 5 to 100 wt % for the particular coupler. To prevent the cyan dye image from being deteriorated by heat, and in particular light, it is more effective to introduce an ultraviolet absorber into the cyan coupler-forming layer and the opposite layers adjacent to the cyan color-forming layers.

As the ultraviolet absorber, aryl-substituted benzotriazole compounds (e.g., those described in U.S. Pat. No. 3,533,794), 4-thiazolidone compounds (e.g., those described in U.S. Pat. Nos. 3,314,794 and 3,352,681), benzophenone compounds (e.g., those described in JP-A No. 2784/1971), cinnamic acid ester compounds (e.g., those described in U.S. Pat. Nos. 3,705,805 and 3,707,395), butadiene compounds (e.g., those described in U.S. Pat. No. 4,045,229), or benzoxazole compounds (e.g., those described in U.S. Pat. No. 3,700,455) can be used. Ultraviolet-absorptive couplers (e.g., α-naphthol type cyan dye forming couplers) and ultraviolet-absorptive polymers can, for example, be used also. These ultraviolet-absorbers may be mordanted in the special layer.

Of these, benzotriazole compounds substituted by an aryl group described above are preferable.

As a binder or a protective colloid that can be used in the emulsion layers of the photographic material of the present invention, gelatin is advantageously used, but other hydrophilic colloids can be used alone or in combination with gelatin.

In the present invention, gelatin may be lime-treated gelatin or acid-processed gelatin. Details of the manufacture of gelatin is described by Arther Veis in *The Macromolecular Chemistry of Gelatin* (published by Academic Press, 1964).

The color-developing solution to be used in the developing process of the photographic material of the present invention is preferably an aqueous alkaline solution whose major component is an aromatic primary amine-type color developing agent. As the color developing agent, aminophenol-type compounds are useful, and p-phenylenediamine-type compounds are preferably used, typical examples thereof being 3-methyl-4-amino-N,N-diethylaniline, 3-methyl-4-amino-N-ethyl-N-$\beta$-hydroxylaniline, 3-methyl-4-amino-N-ethyl-N-$\beta$-methanesulfonamidoethylaniline, and 3-methyl-4-amino-N-ethyl-N-$\beta$-methoxyethylaniline and their sulfates, and hydrochlorides or p-toluenesulfonates. These compounds may be used in combination according to the purpose.

Generally the color-developing solution contains pH buffers such as carbonates, borates, or phosphates of alkali metals; antifoggants or development retarders, such as mercapto compounds, benzothiazoles, benzimidazoles, iodides or bromides; and if required, preservatives such as hydroxylamine, diethylhydroxylamine, sulfites, hydrazines, phenylsemicarbazides, triethanolamine, catecholsulfonic acids, and triethylenediamine (1,4-diazabicyclo[2,2,2]octane); organic solvents such as ethylene glycol and diethylene glycol; development accelerators such as benzyl alcohol, polyethylene glycol, quaternary ammonium salts, and amines; dye-forming couplers; competing couplers; fogging agents such as sodium boron hydride; auxiliary developing agents such as 1-phenyl-3-pyrazolidone: thickening agents; and chelate agents, such as aminopolycarboxylic acids, aminopolyphosphonic acids, alkylphosphonic acids, and phosphonocarboxylic acids such as, for example, ethylenediaminetetraacetic acid, nitrilotriacetic acid, diethylenetriaminetetraacetic acid, cyclohexanediaminetetraacetic acid, hydroxyethylimidinoacetic acid, 1-hydroxyethylidene-1,1-diphosphonic acid, nitrilo-N,N,N-trimethylenephosphonic acid, ethylenediamine-N,N,N',N'-tetramethylenephosphonic acid, and ethylenediamine-di(o-hydroxyphenylacetic acid), and their salts.

For reversal processing, a color development is generally carried out after a black-and white development. For the black-and-white developing solution, known black-and-white-developing agents such as dihydroxybenzenes (e.g., hydroquinone), 3-pyrazolidones (e.g., 1-phenyl-3-pyrazolidone), and aminophenols (e.g., N-methyl-p-aminophenol) may be used alone or in combination with others.

Generally the color-developing solution has a pH of 9 to 12. Although the replenishing amount of the developing solution varies depending on the color photographic material to be processed, generally the replenishing amount is 3 l or below per m$^2$ of the photographic material, and the replenishing amount can be lowered to 500 ml or below if the bromide ion concentration of the replenishing solution is lowered. If it is required to lower the replenishing amount, it is preferable that the area of the processing tank in contact with air is minimized to prevent the solution from evaporating or being oxidized by air. The replenishing amount can also be lowered by suppressing the accumulation of bromide ions in the developing solution.

The photographic emulsion layers are generally subjected to a bleaching process after color development.

The bleaching process can be carried out together with the fixing process (bleach-fixing process), or it can be carried out separately from the fixing process. Further, to quicken the process, bleach-fixing may be carried out after the bleaching process. In accordance with the purpose, the process may be arbitrarily carried out using a bleach-fixing bath having two successive tanks, or a fixing process may be carried out before the bleach-fixing process, or a bleaching process may be carried out after the bleach-fixing process. As the bleaching agent, use can be made of, for example, compounds of polyvalent metals, such as iron (III), cobalt (III), chromium (VI), and copper (II), peracids, quinones, and nitro compound. As typical bleaching agents, use can be made of ferricyanides; dichromates; organic complex salts of iron (II) or cobalt (III), such as complex salts of aminopolycarboxylic acids, for example ethylenediaminetetraacetic acid, diethylenetriamine-tetraacetic acid, cyclohexanediaminetetraacetic acid, methyliminodiacetic acid, 1,3-diaminopropanetetraacetic acid, and glycol ether diamine tetraacetic acid, citric acid, tartaric acid, and malic acid; persulfates; bromates; permanganates; and nitrobenzenes. Of these, aminopolycarboxylic acid iron (III) complex salts, including ethylenediaminetetraacetic acid iron (III) complex salts, including ethylenediaminetetraacetic acid iron (III) complex salt, and persulfates are preferable in view of rapid processing and the prevention of environmental pollution. Further, aminopolycarboxylic acid iron (III) complex salts are particularly useful in a bleaching solution as well as a bleach-fix solution. The pH of the bleaching solution or the bleach-fix solution using these aminopolycarboxylic acid iron (III) complex salts is generally 5.5 to 8, but if it is required to quicken the process, the process can be effected at a lower pH.

In the bleaching solution, the bleach-fix solution, and the baths preceding them a bleach-accelerating solution may be used if necessary. Examples of useful bleach-accelerating agents are compounds having a mercapto group or a disulfide linkage, described in U.S. Pat. No. 3,893,858, West German Pat. No. 1,290,812, JP-A No. 95630/1978, and Research Disclosure No. 17129 (June 1978); thiazolidine derivatives, described in JP-A No. 140129/1975; thiourea derivatives, described in U.S. Pat. No. 3,706,561; iodide salts, described in JP-A No. 16235/1983; polyoxyethylene compounds, described in West German Pat. No. 2,748,430; polyamine compounds, described in JP-B No. 8836/1960; and iodide ions. Of these, compounds having a mercapto group or a disulfide group are preferable in view of higher acceleration effect, and in particular, compounds described in U.S. Pat. No. 3,893,858, West German Pat. No. 1,290,812, and JP-A No. 95630/1978 are preferable. Compounds described in U.S. Pat. No. 4,552,834 are preferable. These bleach-accelerating agents may be added into the photographic material. When the color photographic materials for photographing are to be bleach-fixed, these bleach-accelerating agents are particularly effective.

As fixing agent can be mentioned thiosulfates, thiocyanates, thioether-type compounds, thioureas, and large amounts of iodide salts, though the use of thiosulfates is common, and particularly ammonium thiosulfate can be used most widely. It is preferable to use, as a preservative for the bleach fix solution, sulfites, bisulfites, and carbonyl bisulfite adducts.

It is common for the silver halide color photographic material of the present invention to undergo, after a desilvering process such as fixing or bleach-fix, a washing step and/or a stabilizing step. The amount of washing water may be set within a wide range depending on the characteristics (e.g., due to the materials used, such as couplers), the application of the photographic material, the washing temperature, the number of washing tanks (the number of steps), the type of replenishing system, including, for example, the counter-current system and the direct flow system, and other various conditions. Of these, the relationship between the number of water-washing tanks and the amount of washing water in the multi-stage counter-current system can be found according to the method described in *Journal of the Society of Motion Picture and Television Engineers*, Vol. 64, pages 248 to 253 (May 1955).

According to the multi-stage-counter-current system described in the literature mentioned above, although the amount of washing water can be considerably reduced, bacteria propagate with an increase of retention time of the washing water in the tanks, leading to a problem with the resulting suspend matter adhering to the photographic material. In processing the present color photographic material, as a measure to solve this problem, the method of reducing calcium and magnesium described in JP-A No. 288838/1987 can be used quite effectively. Also chlorine-type bactericides such as sodium chlorinated isocyanurate, cyabendazoles, isothiazolone compounds described in JP-A No. 8542/1982, benzotriazoles, and other bactericides described by Hiroshi Horiguchi in *Bokin Bobaizai no Kaqaku* (1986) published by Sankyo-Shuppan, *Biseibutsu no Mekkin, Sakkin, Bobaigijutsu* (1982), edited by Eiseigijutsu-kai, published by Kogyogijutsu-kai, and in *Bokin Bobaizai Jiten* (1986), edited by Nohon Bokin Bobai-Gakkai, can be used.

The pH of the washing water used in processing the present photographic material is 4 to 9, preferably 5 to 8. The washing water temperature and the washing time to be set may very depending, for example, on the characteristics and the application of the photographic material, and they are generally selected in the range of 15 to 45° C. for 20 sec. to 10 min., and preferably in the range of 25 to 40° C. for 30 sec. to 5 min. Further, the photographic material of the present invention can be processed directly with a stabilizing solution instead of the above washing. In such a stabilizing process, any of known processes, for example, a multi-step counter-current stabilizing process or its low-replenishing-amount process, described in JP-A Nos. 8543/1982, 14834/1983, and 220345/1985, and an ion-exchanging process can be used.

In some cases, the above washing process is further followed by a stabilizing process, and as an example thereof can be mentioned a stabilizing bath that is used as a final bath for color photographic materials for photography, which contains formalin and a surface-active agent. In this stabilizing bath, each kind of the chelating agents and bactericides may be added.

The over-flow solution due to the replenishing of washing solution and/or stabilizing solution may be reused in other steps, such as a desilvering step.

The silver halide color photographic material of the present invention may contain therein a color-developing agent for the purpose of simplifying and quickening the process. To contain such a color-developing agent, it is preferable to use a precursor for a color-developing agent. For example, indoaniline-type compounds described in U.S. Pat. No. 3,342,597, Schiff base-type compounds described in U.S. Pat. No. 3,342,599 and *Research Disclosure* Nos. 14850 and 15159, aldol compounds described in *Research Disclosure* No. 13924, metal salt complexes described in U.S. Pat. No. 3,719,492, and urethane-type compounds described in JP-A No. 135628/1978 can be mentioned.

For the purpose of accelerating the color development, the present silver halide color photographic material may contain, if necessary, various 1-phenyl-3-pyrazolidones. Typical compounds are described in JP-A No. 64339/1981, 144547/1982, and 115438/1983.

The various processing solutions used for the present invention are used at 10 to 50° C. Although generally a temperature of 33 to 38° C. is standard, a higher temperature can be used to accelerate the process to reduce the processing time, or a lower temperature can be used to improve the image quality or the stability of the processing solutions. Also, to save the silver of the photographic material, a process using hydrogen peroxide intensification or cobalt intensification described in West German Pat. No. 2,226,770 and U.S. Pat. No. 3,674,499 may be carried out.

Next, the effects of the present invention will be described in detail in accordance with examples, but the invention is not limited to these examples.

EXAMPLE 1

Monocolor photographic materials (samples 101 to 117) composed including a two layers of emulsion layer and a protective layer having the compositions shown below were each prepared on cellulose triacetate supports. Figures in the compositions are indicated in a coating amount of g/m² except for the couplers, but the coating amount of silver halide emulsion is indicated in terms of silver.

| Emulsion layer | |
|---|---|
| Silver iodobromide emulsion (silver iodide: 2 mol %, average grain size: 3 μm) silver | 0.8 |
| Gelatin | 1.2 |
| Coupler (see Table 1) (in mol/m²) | 0.001 |
| Dibutyl phthalate | 0.3 |
| Protective layer | |
| Gelatin | 0.9 |
| Poly(methyl methacrylate) particle (diameter: 1.5 μm) | 0.4 |
| Sodium 1-oxy-3,5-dichloro-s-triazinic acid | 0.04 |

Next, Sample 118 was prepared in the same manner as Sample 114, except that dibutyl phthalate was not added.

Thus-prepared color photographic materials (Samples 101 to 118) were subjected to the standard color development described below after the exposure of light at an exposure density of 40 cms through an wedge having a continuous density.

| Standard color development (temperature: 38° C.) | |
|---|---|
| Color development | 3 min. 15 sec. |
| Bleaching | 6 min. 30 sec. |
| Fixing | 4 min. 20 sec. |
| Water washing | 5 min. |
| Stabilizing | 1 min. |

Compositions of the processing solutions used in each processing step were as follows:

Color developer

| -continued | |
|---|---|
| Diethylenetriaminepentaacetic acid | 1.0 g |
| 1-Hydroxyethylidene-1,1-diphosphonic acid | 2.0 g |
| Sodium sulfite | 4.0 g |
| Potassium carbonate | 30.0 g |
| Potassium bromide | 1.4 g |
| Potassium iodide | 1.3 mg |
| Hydroxylamine sulfonate | 2.4 g |
| 4-(N-ethyl-N-β-hydroxyethylamino)-2-methylaniline sulfonate | 4.5 g |
| Water to make | 1000 ml |
| pH | 10.0 |
| Bleaching solution | |
| Fe(III) ammonium salt of 1,3-diaminopropanetetraacetic acid | 105.0 g |
| Aqueous ammonia | 3.0 ml |
| Ammonium bromide | 150.0 g |
| Ammonium nitrate | 10.0 g |
| Water to make | 1000 ml |
| pH | 4.2 |
| Fixing solution | |
| Disodium ethylenediaminetetraacetate | 1.0 g |
| Sodium sulfite | 4.0 g |
| Ammonium thiosulfite aqu. solution (70%) | 175.0 ml |
| Sodium bisulfite | 4.6 g |
| Water to make | 1000 ml |
| pH | 6.6 |
| Stabilizing solution | |
| Formalin (40%) | 2.0 ml |
| Polyoxyethylene-p-monononylphenyl ether (average polymerization degree: about 10) | 0.3 g |
| Water to make | 1000 ml |

Samples (101 to 118) cyan-colored by the standard color development processing were measured for a gamma value (the gradient of sensitometory) and Dmax (maximum color density) by using a Fuji Densitometer (FSD). Results are shown in Table 1. Each value is designated a relative value with the value of sample 101 assumed to be 1.

TABLE 1

| Sample | Coupler | G-value | Dmax |
|---|---|---|---|
| 101 | A (Comparative coupler) | 1.00 | 1.00 |
| 102 | B (Comparative coupler) | 0.85 | 0.98 |
| 103 | C (Comparative coupler) | 0.92 | 0.89 |
| 104 | D (Comparative coupler) | 0.77 | 1.01 |
| 105 | E (Comparative coupler) | 0.84 | 0.83 |
| 106 | F (Comparative coupler) | 0.90 | 0.95 |
| 107 | G (Comparative coupler) | 1.32 | 1.31 |
| 108 | H (Comparative coupler) | 1.50 | 1.38 |
| 109 | I (Comparative coupler) | 2.15 | 1.81 |
| 110 | J (Comparative coupler) | 1.44 | 1.24 |
| 111 | 4 (This Invention) | 1.56 | 1.56 |
| 112 | 5 (This Invention) | 1.42 | 1.52 |
| 113 | 6 (This Invention) | 1.58 | 1.63 |
| 114 | 7 (This Invention) | 1.65 | 1.70 |
| 115 | 24 (This Invention) | 1.72 | 1.67 |
| 116 | 25 (This Invention) | 1.61 | 1.58 |
| 117 | 41 (This Invention) | 1.59 | 1.55 |
| 118 | 7 (This Invention) | 1.57 | 1.61 |

Couplers used in this Example and in the following Examples are as follows:

(A) Compound described in U.S. Pat. No. 4,333,999

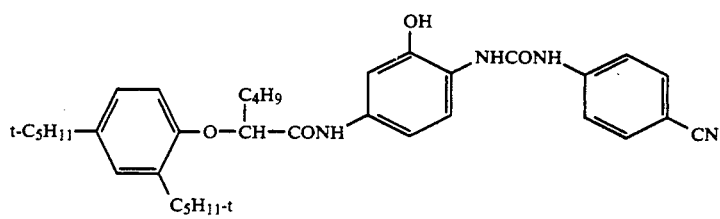

(B) Compound described in JP-A No. 204545/1982

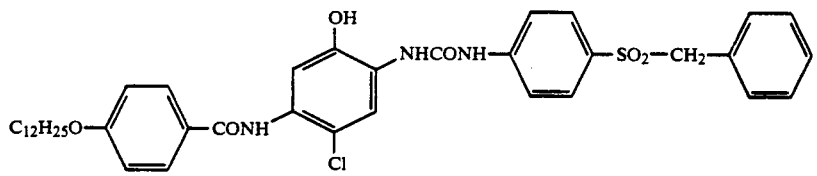

(C) Compound described in JP-A No. 201657/1989

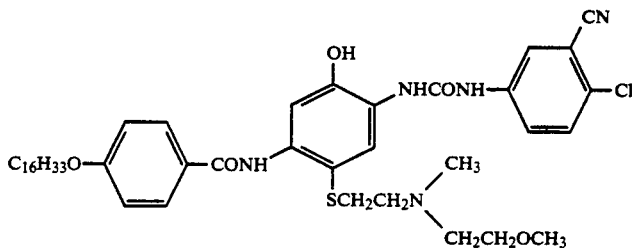

(D) Compound described in JP-A No. 219749/1989

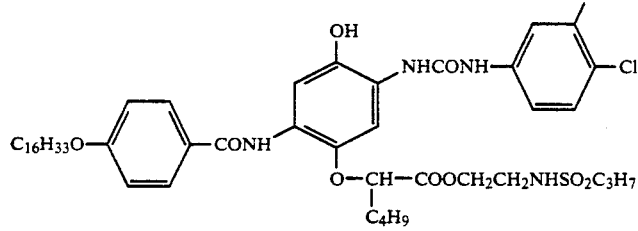
(E) Compound described in JP-A No. 46644/1984
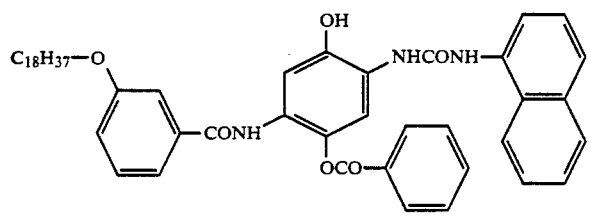
(F) Compound described in JP-A No. 33251/1983
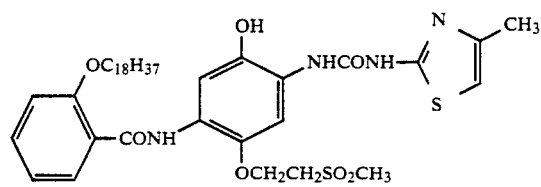
(G) Compound described in U.S. Pat. No. 4,753,871
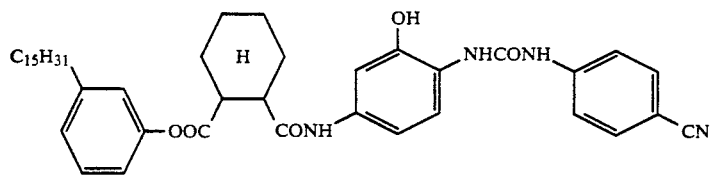
(H) Compound described in European Patent No. 271,323
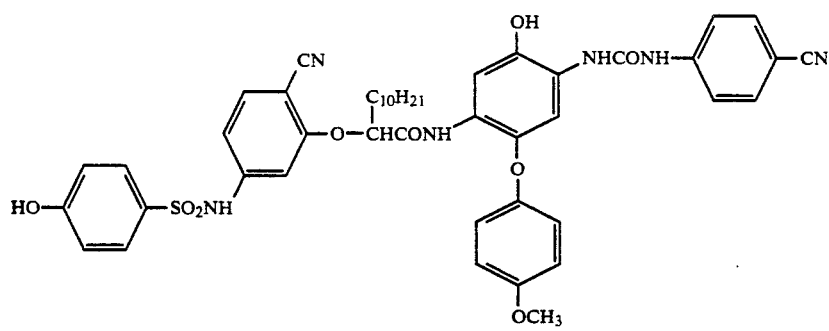
(I) Compound described in U.S. Pat. No. 4,775,616
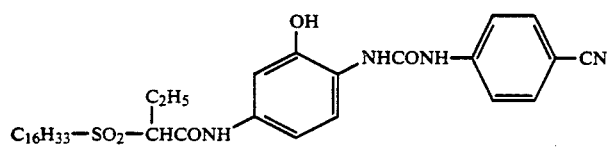
(J)

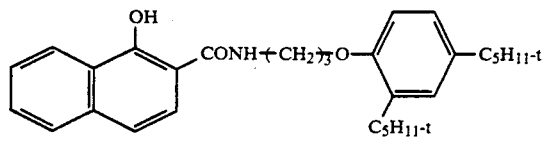

As is apparent from the results in Table 1, it can be noted that when the compound of the present invention is used, coupling reactivity and color density are high compared with those that obtained by using comparative coupler A, B, C, D, E, or F.

Next, Samples 107 to 118 were evaluated for λmax (maximum absorbance), fastness to heat, and reduction fastness.

λmax was determined by using a Hitachi UV-visible Spectrophotometer Model U-3200 (made by Hitachi Seisakusho).

Fastness to heat was determined as a remaining ratio (%) of image dye density after heating cyan colored samples (107 to 118) for 7 days at 80° C. and 70% RH as compared with an initial density of 1.5:

Remaining ratio = (density after heating/1.5) × 100

Next, samples 107 to 118 were subjected to an exposure to light through an continuous wedge at a exposure density of 40 cms and then to the same processing as the above-described standard color development processing, except that the bleaching solution having the composition shown below was used (hereinafter referred to as reduction fading processing), to evaluate the resistance to reduction fading processing.

| Bleaching solution | |
|---|---|
| Fe(III) ammonium salt of 1,3-diamino-propanetetraacetic acid | 90 g |
| Fe(II) ammonium salt of 1,3-diamino-propanetetraacetic acid | 15 g |
| Aqueous ammonia | 3 ml |
| Ammonium bromide | 150 g |
| Ammonium nitrate | 10 g |
| Water to make | 1000 ml |
| pH | 4.2 |

Each Dmax (maximum density of color) of cyan-colored samples (107 to 118) after reduction fading processing was determined by using a Fuji Densitometer (FSD) and the ratio of this value to the corresponding Dmax after standard color development processing was calculated.

Resistance to reduction fading (%) = (Dmax after standard processing/Dmax after reduction fading processing) × 100

The thus-obtained G-value, Dmax, λmax, remaining ratio of image dye, and resistance to reduction discoloring are shown in Table 2.

TABLE 2

| Sample No. | Coupler | λmax | Remaining Ratio (%) | Resistance to Reduction Fading (%) |
|---|---|---|---|---|
| 107 | G (Comparative) | 681 | 93 | 93 |
| 108 | H (Comparative) | 692 | 85 | 82 |
| 109 | I (Comparative) | 687 | 86 | 81 |
| 110 | J (Comparative) | 697 | 62 | 58 |
| 111 | 4 (This Invention) | 700 | 97 | 96 |
| 112 | 5 (This Invention) | 698 | 96 | 95 |
| 113 | 6 (This Invention) | 697 | 96 | 99 |
| 114 | 7 (This Invention) | 702 | 98 | 99 |
| 115 | 24 (This Invention) | 701 | 97 | 94 |
| 116 | 25 (This Invention) | 703 | 96 | 95 |
| 117 | 41 (This Invention) | 699 | 96 | 96 |
| 118 | 7 (This Invention) | 693 | 99 | 99 |

As is apparent from the results in Table 2, it can be understood that when the compounds of the present invention were used, λmax of the color dyes formed were in the range of 685 to 705 nm where is suitable for a negative photographic material for photographing and the preservability of the image dye and resistance to reduction discoloring were superior as compared with those using comparative couplers G, H, I, and J.

EXAMPLE 2

Samples of mono-color photographic material (201 to 217) were prepared in the same manner as in Example 1, except that cyan couplers were changed to as shown in Table 3, respectively. Gamma-value and Dmax of each sample thus-prepared were determined in the same manner as in Example 1 and the results are shown in Table 3.

TABLE 3

| Sample No. | Coupler | G-value | Dmax |
|---|---|---|---|
| 201 | A (Comparative) | 1.00 | 1.00 |
| 202 | B (Comparative) | 0.82 | 0.83 |
| 203 | C (Comparative) | 0.88 | 0.86 |
| 204 | 102 (This Invention) | 1.23 | 1.25 |
| 205 | 103 (This Invention) | 1.31 | 1.29 |
| 206 | 104 (This Invention) | 1.25 | 1.26 |
| 207 | 105 (This Invention) | 1.24 | 1.23 |
| 208 | 106 (This Invention) | 1.78 | 1.30 |
| 209 | 107 (This Invention) | 1.19 | 1.20 |
| 210 | 109 (This Invention) | 1.32 | 1.31 |
| 211 | 113 (This Invention) | 1.20 | 1.22 |
| 212 | 121 (This Invention) | 1.80 | 1.25 |
| 213 | 122 (This Invention) | 1.75 | 1.21 |
| 214 | 123 (This Invention) | 1.95 | 1.26 |
| 215 | 124 (This Invention) | 1.72 | 1.19 |
| 216 | 129 (This Invention) | 1.76 | 1.23 |
| 217 | 131 (This Invention) | 1.69 | 1.24 |

As is apparent from the results in Table 3, it can be understood that the gamma-values and maximum color densities of the samples of this invention were higher than those of the comparative couplers.

EXAMPLE 3

Multilayer color photographic materials (Sample 301 to 310) were prepared by the multi-coating of each layer having a composition shown below on a prime-coated triacetate cellulose film base.

Composition of Photosensitive Layer

The figure corresponding to each component is indicated in a coating amount of the $g/m^2$, but the coating amount of silver halide emulsion is indicated in terms of silver. With respect to the sensitizing dye, the coating amount is indicated in mol per mol of silver halide in the same layer.

| (Sample 101) | |
|---|---|
| First layer (Halation preventing layer) | |
| Black colloidal silver silver | 0.18 |
| Gelatin | 0.34 |
| Second layer (Intermediate layer) | |
| 2,5-Di-t-pentadecylhydroquinone | 0.18 |
| EX-1 | 0.07 |
| EX-3 | 0.02 |
| EX-12 | 0.002 |
| U-1 | 0.06 |
| U-2 | 0.08 |
| U-3 | 0.10 |
| HBS-1 | 0.10 |
| HBS-2 | 0.02 |
| Gelatin | 0.88 |
| Third layer (First red-sensitive emulsion layer) | |
| Emulsion A silver | 0.25 |
| Emulsion B silver | 0.25 |
| Sensitizing dye I | $6.9 \times 10^{-5}$ |
| Sensitizing dye II | $1.8 \times 10^{-5}$ |
| Sensitizing dye III | $3.1 \times 10^{-4}$ |
| Coupler (see Table 4) | $3.1 \times 10^{-4}$ $(mol/m^2)$ |
| EX-10 | 0.020 |
| HBS-1 | 0.060 |
| Gelatin | 0.73 |
| Fourth layer (Second red-sensitive emulsion layer) | |
| Emulsion G silver | 1.0 |
| Sensitizing dye I | $5.1 \times 10^{-5}$ |
| Sensitizing dye II | $1.4 \times 10^{-5}$ |
| Sensitizing dye III | $2.3 \times 10^{-4}$ |
| Coupler (see Table 4) | $7.5 \times 10^{-4}$ $(mol/m^2)$ |
| EX-3 | 0.020 |
| EX-4 | 0.030 |
| EX-10 | 0.015 |
| HBS-1 | 0.060 |
| Gelatin | 1.10 |
| Fifth layer (Third red-sensitive emulsion layer) | |
| Emulsion D silver | 1.60 |
| Sensitizing dye I | $5.4 \times 10^{-5}$ |
| Sensitizing dye II | $1.4 \times 10^{-5}$ |
| Sensitizing dye III | $2.4 \times 10^{-4}$ |
| EX-3 | 0.010 |
| EX-4 | 0.080 |
| EX-2 | 0.097 |
| HBS-1 | 0.22 |
| HBS-2 | 0.10 |
| Gelatin | 1.39 |
| Sixth layer (Intermediate layer) | |
| EX-5 | 0.040 |
| HBS-1 | 0.020 |
| Gelatin | 0.68 |
| Seventh layer (First green-sensitive emulsion layer) | |
| Emulsion A silver | 0.15 |
| Emulsion B silver | 0.15 |
| Sensitizing dye V | $3.0 \times 10^{-5}$ |
| Sensitizing dye VI | $1.0 \times 10^{-4}$ |
| Sensitizing dye VII | $3.8 \times 10^{-4}$ |
| EX-6 | 0.260 |
| EX-1 | 0.021 |
| EX-7 | 0.030 |
| EX-8 | 0.025 |
| HBS-1 | 0.100 |
| HBS-3 | 0.010 |
| Gelatin | 0.53 |
| Eighth layer (Second green-sensitive emulsion layer) | |
| Emulsion C silver | 0.45 |
| Sensitizing dye V | $2.1 \times 10^{-5}$ |
| Sensitizing dye VI | $7.0 \times 10^{-5}$ |
| Sensitizing dye VII | $2.6 \times 10^{-4}$ |
| EX-6 | 0.094 |
| EX-8 | 0.018 |
| EX-7 | 0.026 |
| HBS-1 | 0.160 |
| HBS-3 | 0.008 |
| Gelatin | 0.43 |
| Ninth layer (Third green-sensitive emulsion layer) | |
| Emulsion D silver | 1.2 |
| Sensitizing dye V | $3.5 \times 10^{-5}$ |
| Sensitizing dye VI | $8.0 \times 10^{-5}$ |
| Sensitizing dye VII | $3.0 \times 10^{-4}$ |
| EX-13 | 0.015 |
| EX-14 | 0.015 |
| EX-11 | 0.100 |
| EX-1 | 0.025 |
| HBS-1 | 0.25 |
| HBS-2 | 0.10 |
| Gelatin | 1.31 |
| Tenth layer (Yellow filter layer) | |
| Yellow colloidal silver silver | 0.05 |
| EX-5 | 0.08 |
| HBS-1 | 0.03 |
| Gelatin | 0.81 |
| Eleventh layer (First blue-sensitive layer) | |
| Emulsion A silver | 0.08 |
| Emulsion B silver | 0.07 |
| Emulsion F silver | 0.07 |
| Sensitizing dye VIII | $3.5 \times 10^{-4}$ |
| EX-9 | 0.721 |
| EX-8 | 0.042 |
| HBS-1 | 0.28 |
| Gelatin | 0.94 |
| Twelfth layer (Second blue-sensitive emulsion layer) | |
| Emulsion G silver | 0.45 |
| Sensitizing dye VIII | $2.1 \times 10^{-4}$ |
| EX-9 | 0.154 |
| EX-10 | 0.007 |
| HBS-1 | 0.05 |
| Gelatin | 0.66 |
| Thirteenth layer (Third blue sensitive emulsion layer) | |
| Emulsion H silver | 0.77 |
| Sensitizin dye VIII | $2.2 \times 10^{-4}$ |
| EX-15 | 0.20 |
| HBS-1 | 0.07 |
| Gelatin | 0.69 |
| Fourteenth layer (First protective layer) | |
| Emulsion I silver | 0.5 |
| U-4 | 0.11 |
| U-5 | 0.17 |
| HBS-1 | 0.05 |
| Gelatin | 0.85 |
| Fifteenth layer (Second protective layer) | |
| Poly(methyl methacrylate) particle (diameter: about 1.5 μm) | 0.54 |
| S-1 | 0.20 |
| Gelatin | 1.20 |

In each layer gelatin hardener H and surface-active agent were added in addition to the above components.

| Emulsion | Average AgI Content (%) | Grain Size Average Diameter (μm) | Deviation Coefficient (%) | Ratio of Diameter/ Thickness | Ratio of Silver Amount (AgI content %) | |
|---|---|---|---|---|---|---|
| A | 4.1 | 0.45 | 27 | 1 | Core/Shell = 1/3(13/1) | Double Structure Grains |
| B | 8.9 | 0.70 | 14 | 1 | Core/Shell = 3/7(25/2) | Double Structure Grains |
| C | 10 | 0.75 | 30 | 2 | Core/Shell = 1/2(24/3) | Double Structure Grains |
| D | 16 | 1.05 | 35 | 2 | Core/Shell = 1/2(40/0) | Double Structure Grains |
| E | 10 | 1.05 | 35 | 3 | Core/Shell = 1/2(24/3) | Double Structure Grains |
| F | 4.1 | 0.25 | 28 | 1 | Core/Shell = 1/3(13/1) | Double Structure Grains |
| G | 13.6 | 0.75 | 25 | 2 | Core/Shell = 1/2(40/0) | Double Structure Grains |
| H | 14 | 1.30 | 25 | 3 | Core/Shell = 37/63(34/2) | Double Structure Grains |
| I | 1 | 0.07 | 15 | 1 | Uniform Grains | |

EX-1

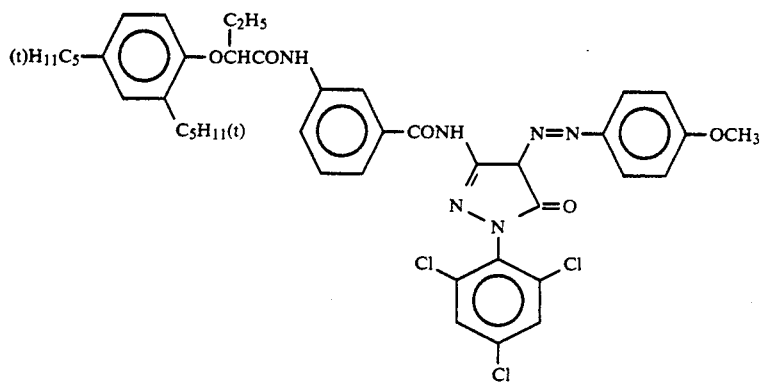

EX-2

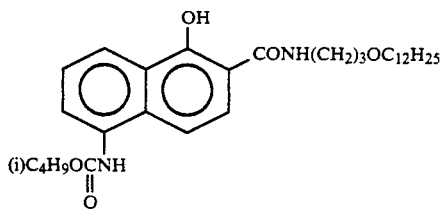

EX-3

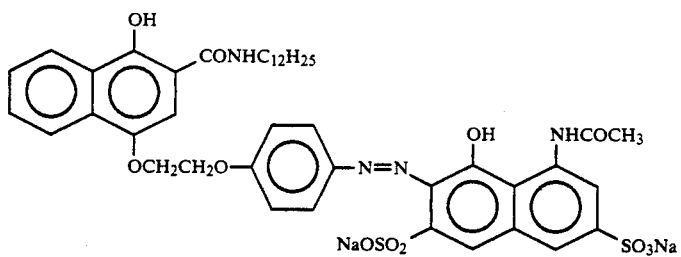

EX-4

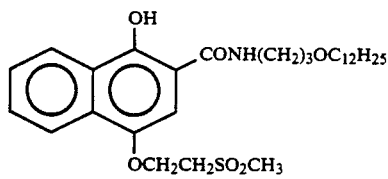

EX-5

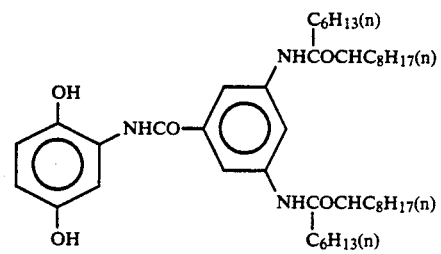

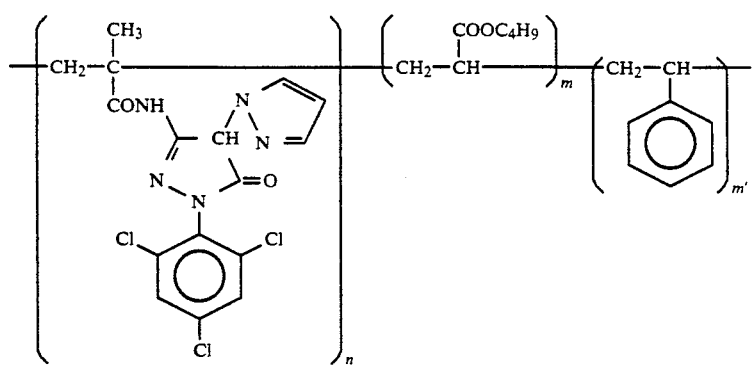
EX-6
n = 50
m = 25
m' = 25
mol. wt. about 20,000
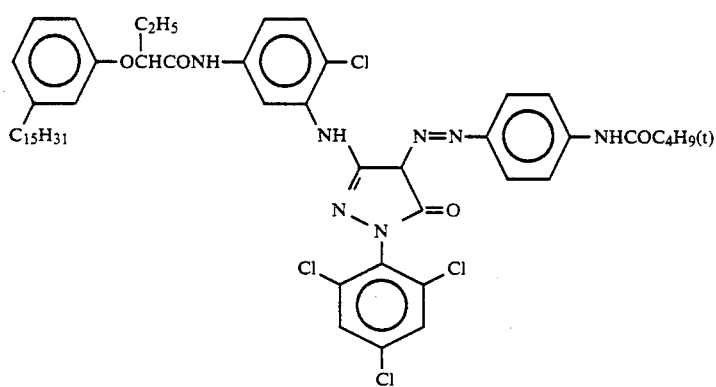
EX-7
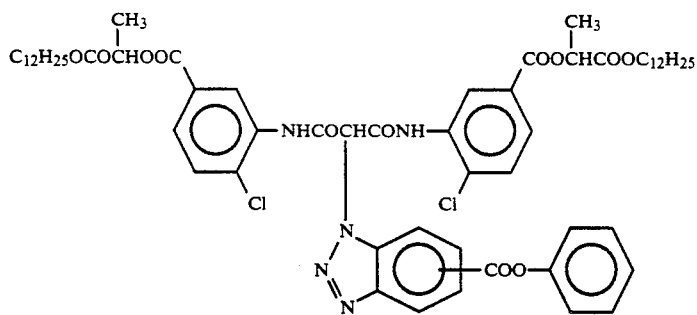
EX-8
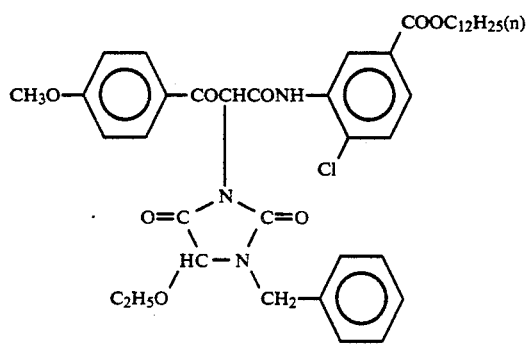
EX-9

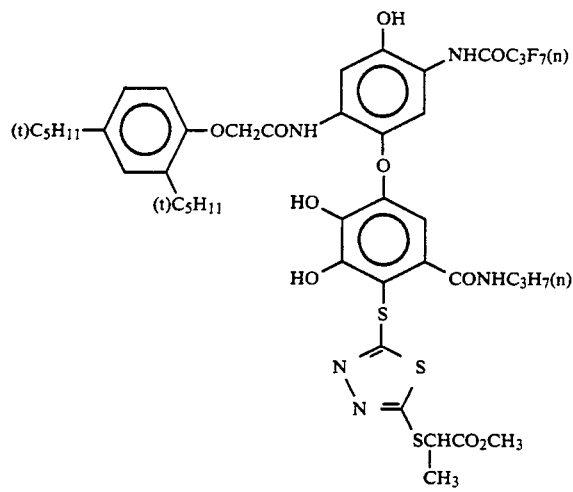
EX-10
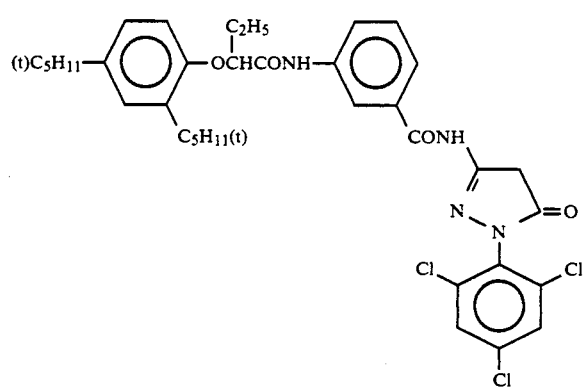
EX-11
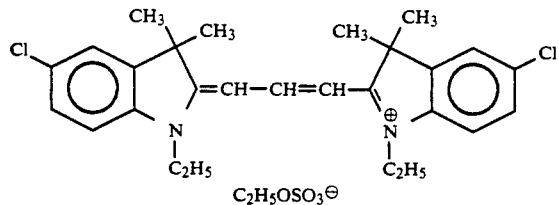
EX-12
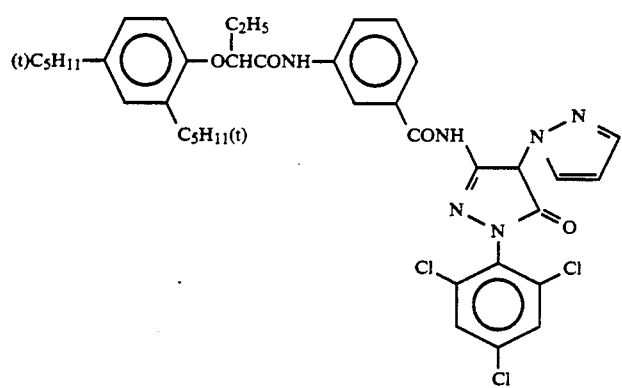
EX-13

-continued
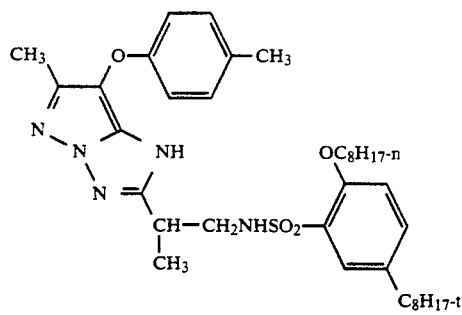
EX-14
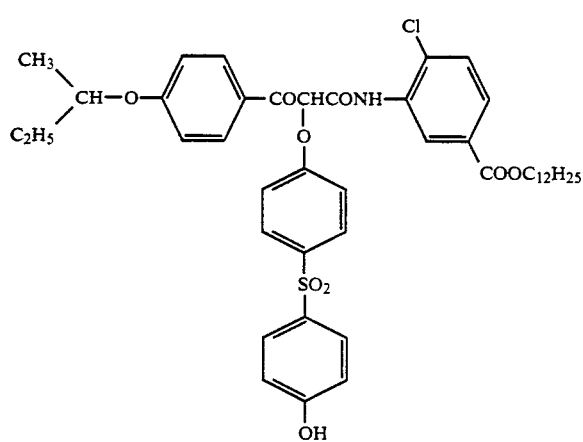
EX-15
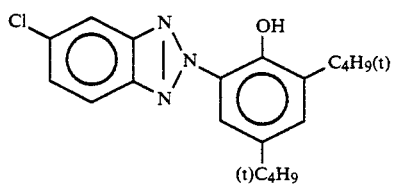
U-1
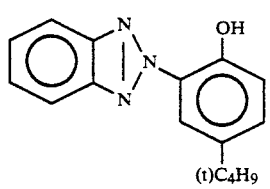
U-2
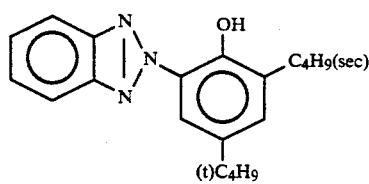
U-3
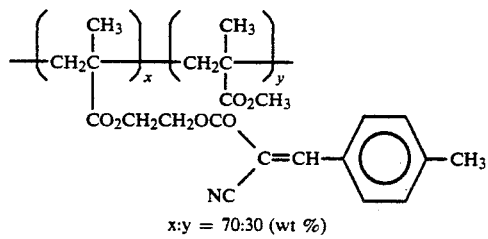
U-4

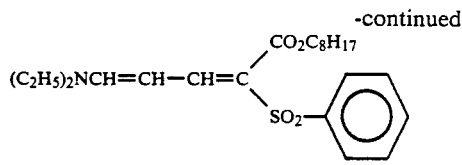
U-5
Tricresyl phosphate    HBS-1
Di-n-butyl phthalate    HBS-2
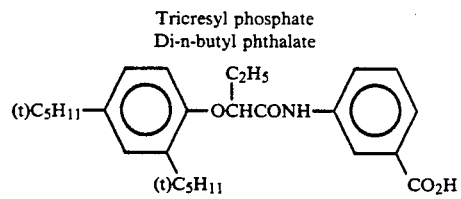
HBS-3
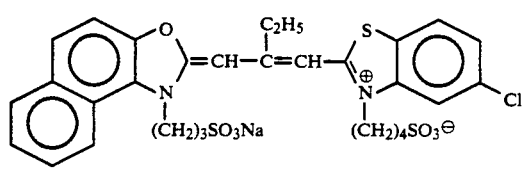
Sensitizing Dye I
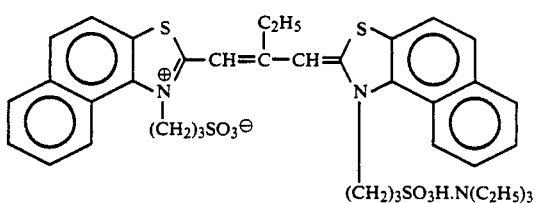
Sensitizing Dye II
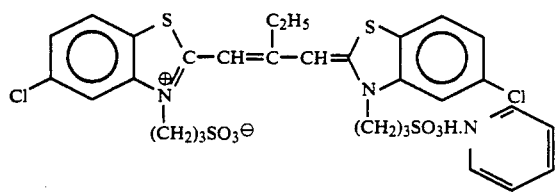
Sensitizing Dye III
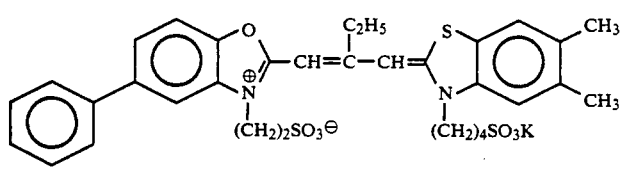
Sensitizing Dye V
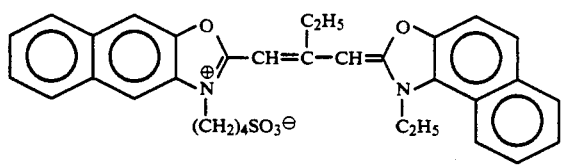
Sensitizing Dye VI
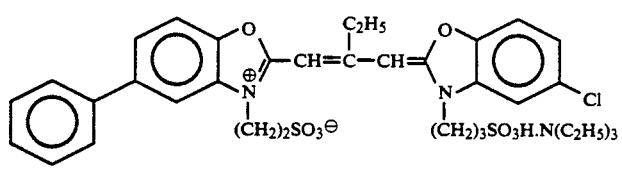
Sensitizing Dye VII
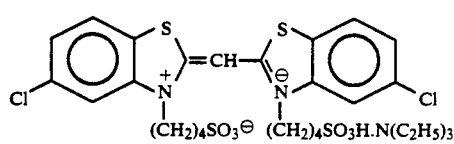
Sensitizing Dye VIII

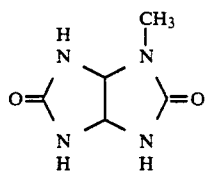 S-1

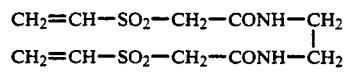 H-1

Thicknesses of dried layer excluding prime-coatings and support base of these samples 301 to 310 were in the range of 16.5 μm to 17.4 μm.

The thus-prepared samples were converted to 35 mm width strip by cutting and then subjected to an exposure to red light and to a development processing process described below by an automatic processor for cine. Samples to be evaluated for their performance were processed after the accumulated replenishing amount of color developer reached to three times that of the tank of mother solution.

Processing Process

| Process | Time | Temperature | Replenisher Amount* | Tank Volume |
|---|---|---|---|---|
| Color development | 3 min. 15 sec. | 37.8° C. | 23 ml | 10 l |
| Bleaching | 40 sec. | 38.0° C. | 5 ml | 5 l |
| Fixing | 1 min. 30 sec. | 38.0° C. | 30 ml | 10 l |
| Water washing (1) | 30 sec. | 38.0° C. | — | 5 l |
| Water washing (2) | 30 sec. | 38.0° C. | 30 ml | 5 l |
| Stabilizing | 30 sec. | 38.0° C. | 20 ml | 5 l |
| Drying | 1 min. | 55° C. | | |

Note:
*Replenisher amount per 1 meter length of 35 mm width

Water washing steps were carried out in a countercurrent mode from the tank of water washing (2) to the tank of water washing (1).

The compositions of each processing solution were as follows:

| Color developer | Mother solution (g) | Replenisher (g) |
|---|---|---|
| Diethylenetriaminepentaacetic acid | 1.0 | 1.1 |
| 1-Hydroxyethylidene-1,1-diphosphonic acid | 3.0 | 3.2 |
| Sodium sulfite | 4.0 | 4.9 |
| Potassium carbonate | 30.0 | 30.0 |
| Potassium bromide | 1.4 | — |
| Potassium iodide | 1.5 mg | — |
| Hydroxylamine sulfate | 2.4 | 3.6 |
| 2-Methyl-4-N-[N-ethyl-N-(β-hydroxyethyl)-amino]aniline sulfonate | 4.5 | 6.4 |
| Water to make | 1.0 l | 1.0 l |
| pH | 10.05 | 10.10 |

| Bleaching solution | Mother solution (g) | Replenisher (g) |
|---|---|---|
| Iron (III) ammonium 1,3-propylenediamine tetraacetate monohydrate | 144.0 | 206.0 |
| 1,3-Propylenediaminetetraacetic acid | 2.8 | 4.0 |
| Ammonium bromide | 84.0 | 120.0 |
| Ammonium nitrate | 30.0 | 41.7 |
| Acetic acid (98%) | 50.0 | 72.5 |
| Water to make | 1.0 l | 1.0 l |
| pH (adjusted by aqueous ammonia) | 4.0 | 3.2 |

| Fixing solution (Both mother solution and replenisher) | (g) |
|---|---|
| Diammonium ethylenediaminetetraacetate | 1.7 |
| Ammonium sulfite | 14.0 |
| Ammonium thiosulfite (700 g/l solution) | 340.0 ml |
| Water to make | 1.0 l |
| pH | 7.0 |

Washing water (Both mother solution and replenisher)

Tap water was treated by passing through a mixed bed ion-exchange column filled with H-type strong acidic cation exchange resin (Amberlite IR-120-B, tradename, made by Rohm & Haas) and OH-type strong basic anion exchange resin (Amberlite IRA-400, the same the above) so that the concentrations of calcium ions and magnesium ions decrease both to 3 mg/m² or below. To the thus-obtained ion-exchanged water 20 mg/l of sodium dichlorinated isocyanurate and 150 mg/l of sodium sulfate were added. The pH of this water was in a range of 6.5 to 7.5.

| Stabilizing solution (Both mother solution and replenisher) | (g) |
|---|---|
| Formalin (37%) | 1.2 ml |
| Surface-active agent [C$_{10}$H$_{21}$—O—(CH$_2$CH$_2$O)$_{10}$—H] | 0.4 |
| Ethyleneglycol | 1.0 |
| Water to make | 1.0 l |
| pH | 5.0–7.0 |

In the processing process, samples (301 to 310) each exhibit good color-forming and hue, and enough Dmax.

To evaluate the fastness to heat of cyan colored samples (301 to 310), remaining ratio of color image was determined in the same manner as in Example 1.

Next, each two sheets of samples 301 to 310 were subjected to an exposure to red-light through a continuous wedge and then one of the sheets was subjected to a standard color development processing and another was subjected to a reduction discoloring processing, respectively in the same manner as described in Example 1, thereby determining the resistance to reduction discoloring.

The thus obtained remaining ratio of image dye and resistance to reduction fading are shown in Table 4.

TABLE 4

| Sample No. | Coupler | Remaining Ratio (%) | Resistance to Reduction Fading (%) |
|---|---|---|---|
| 301 | H (Comparative) | 87 | 83 |
| 302 | I (Comparative) | 87 | 82 |

TABLE 4-continued

| Sample No. | Coupler | Remaining Ratio (%) | Resistance to Reduction Fading (%) |
|---|---|---|---|
| 303 | J (Comparative) | 69 | 63 |
| 304 | 4 (This Invention) | 98 | 96 |
| 305 | 5 (This Invention) | 96 | 95 |
| 306 | 6 (This Invention) | 97 | 98 |
| 307 | 7 (This Invention) | 97 | 99 |
| 308 | 24 (This Invention) | 98 | 95 |
| 309 | 25 (This Invention) | 95 | 95 |
| 310 | 41 (This Invention) | 96 | 96 |

EXAMPLE 4

Multilayer silver halide photographic materials (Samples 401 to 417) were prepared in the same procedure as in Example 3, except that cyan couplers as shown in Table 5 were used, respectively, and each density was measured. Results are shown in Table 5.

TABLE 5

| Sample No. | Coupler | Density |
|---|---|---|
| 401 | A (Comparative) | 1.00 |
| 402 | B (Comparative) | 0.95 |
| 403 | C (Comparative) | 0.96 |
| 404 | 102 (This Invention) | 1.17 |
| 405 | 103 (This Invention) | 1.19 |
| 406 | 104 (This Invention) | 1.17 |
| 407 | 105 (This Invention) | 1.16 |
| 408 | 106 (This Invention) | 1.20 |
| 409 | 107 (This Invention) | 1.14 |
| 410 | 109 (This Invention) | 1.21 |
| 411 | 113 (This Invention) | 1.13 |
| 412 | 121 (This Invention) | 1.15 |
| 413 | 122 (This Invention) | 1.13 |
| 414 | 123 (This Invention) | 1.16 |
| 415 | 124 (This Invention) | 1.10 |
| 416 | 129 (This Invention) | 1.13 |
| 417 | 131 (This Invention) | 1.14 |

As is apparent from the results in Table 5, it can be understood that samples of the present invention each attained a high color forming property.

EXAMPLE 5

Photographic materials (Samples 501 to 503) were prepared in the same procedure as Sample 111 in Example 1, except that couplers 11, 34, and 35 each were used in a defined amount instead of coupler 4 in Sample 111. These samples were subjected to the same sensitometry as in Example 1 and the same superior gamma values and Dmaxs as Sample 111 were obtained.

EXAMPLE 6

Multilayer color photographic papers (Samples 601 to 617) were prepared by multi-coatings composed of the following layer composition on a two-side polyethylene laminated paper support. Coating solutions were prepared as follows:

Preparation of the First Layer Coating Solution

To a mixture of 19.1 g of yellow coupler (ExY), 4.4 g of image-dye stabilizer (Cpd-1) and 0.7 g of image-dye stabilizer (Cpd-7), 27.2 ml of ethyl acetate and 8.2 g of solvent (Solv-1) were added and dissolved. The resulting solution was dispersed and emulsified in 185 ml of 10% aqueous gelatin solution containing 8 ml of sodium dodecylbenzenesulfonate. Separately another emulsion was prepared by adding two kinds of blue-sensitive sensitizing dye, shown below, to a blend of silver chlorobromide emulsions (cubic grains, 3 : 7 (silver mol ratio) blend of grains having 0.88 μm and 0.7 μm of average grain size, and 0.08 and 0.10 of deviation coefficient of grain size distribution, respectively, each in which 0.2 mol % of silver bromide was located at the surface of grains) in such amounts that each dye corresponds $2.0 \times 10^{-4}$ mol to the large size emulsion and $2.5 \times 10^{-4}$ mol to the small size emulsion, per mol of silver, and then sulfur-sensitized. sensitized. The thus-prepared emulsion and the above-obtained emulsified dispersion were mixed together and dissolved to give the composition shown below, thereby preparing the first layer coating solution.

Coating solutions for the second to seventh layers were also prepared in the same manner as the first-layer coating solution. As a gelatin hardener for the respective layers, 1-hydroxy-3,5-dichloro-s-treazine sodium salt was used.

As spectral-sensitizing dyes for the respective layers, the following compounds were used:

Blue-sensitive emulsion layer:

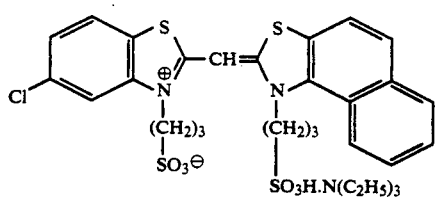

and

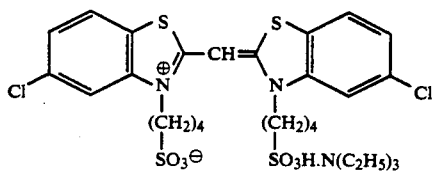

(each $2.0 \times 10^{-4}$ mol to the large size emulsion and $2.5 \times 10^{-4}$ mol to the small size emulsion, per mol of silver halide.)

Green-sensitive emulsion layer:

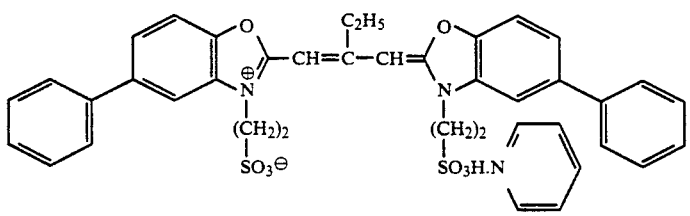

(4.0 × 10$^{-4}$ mol to the large size emulsion and 5.6 × 10$^{-4}$ mol to the small size emulsion, per mol of silver halide)

and

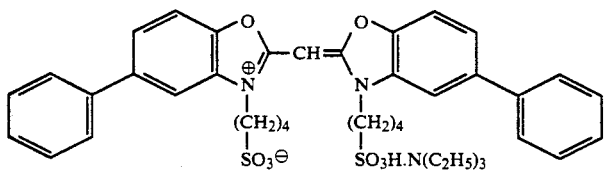

(7.0 × 10$^{-5}$ mol to the large size emulsion and 1.0 × 10$^{-5}$ mol to the small size emulsion, per mol of silver halide)

Red-sensitive emulsion layer:

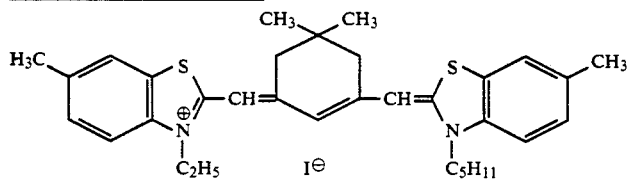

(0.9 × 10$^{-4}$ mol to the large size emulsion and 1.1 × 10$^{-4}$ mol to the small size emulsion, per mol of silver halide)

To the red-sensitive emulsion layer, the following compound was added in an amount of 2.6×10$^{-3}$ mol per mol of silver halide:

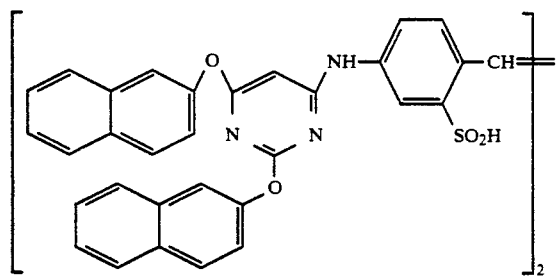

Further, 1-(5-methylureidophenyl)-5-mercaptotetrazole was added to the blue-sensitive emulsion layer, the green-sensitive emulsion layer, and the red-sensitive emulsion layer in amount of 8.5×10$^{-5}$ mol, 7.0×10$^{-4}$ mol, and 2.5×10$^{-4}$ mol, per mol of silver halide, respectively.

The dyes shown below were added to the emulsion layers for prevention of irradiation.

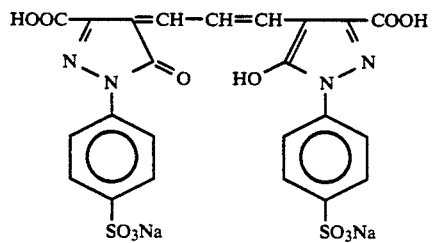

and

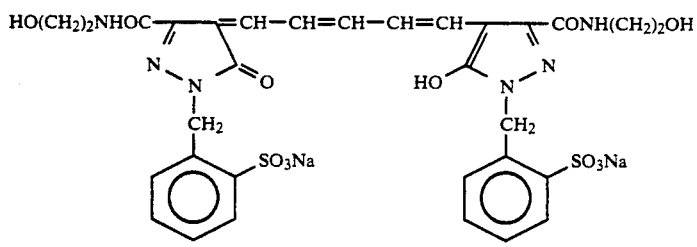

Composition of Layers

The composition of each layer is shown below. The figures represent coating amount (g/m²). The coating amount of each silver halide emulsion is given in terms of silver.

| Supporting Base | |
|---|---|
| Paper laminated on both sides with polyethylene (a white pigment, TiO₂, and a bluish dye, ultra-marine, were included in the first layer side of the polyethylene-laminated film) | |
| First Layer (Blue-sensitive emulsion layer): | |
| The above-described silver chlorobromide emulsion | 0.30 |
| Gelatin | 1.86 |
| Yellow coupler (ExY) | 0.82 |
| Image-dye stabilizer (Cpd-1) | 0.19 |
| Solvent (Solv-1) | 0.35 |
| Image-dye stabilizer (Cpd-7) | 0.06 |
| Second Layer (Color-mix preventing layer): | |
| Gelatin | 0.99 |
| Color mix inhibitor (Cpd-5) | 0.08 |
| Solvent (Solv-1) | 0.16 |
| Solvent (Solv-4) | 0.08 |
| Third Layer (Green-sensitive emulsion layer): | |
| Silver chlorobromide emulsions (cubic grains, 1:3 (Ag mol ratio) blend of grains having 0.55 μm and 0.39 μm of average grain size, and 0.10 and 0.08 of deviation coefficient of grain size distribution, respectively, each in which 0.8 mol % of AgBr was located at the surface of grains) | 0.12 |
| Gelatin | 1.24 |
| Magenta coupler (ExM) | 0.20 |
| Image-dye stabilizer (Cpd-2) | 0.03 |
| Image-dye stabilizer (Cpd-3) | 0.15 |
| Image-dye stabilizer (Cpd-4) | 0.02 |
| Image-dye stabilizer (Cpd-9) | 0.02 |
| Solvent (Solv-2) | 0.40 |
| Fourth Layer (Ultraviolet absorbing layer): | |
| Gelatin | 1.58 |
| Ultraviolet absorber (UV-1) | 0.47 |
| Color-mix inhibitor (Cpd-5) | 0.05 |
| Solvent (Solv-5) | 0.24 |
| Fifth Layer (Red-sensitive emulsion layer): | |
| Silver chlorobromide emulsions (cubic grains, 1:4 (Ag mol ratio) blend of grains having 0.58 μm and 0.45 μm of average grain size, and 0.09 and 0.11 of deviation coefficient of grain size distribution, respectively, each in which 0.6 mol % of AgBr was located at the surface of grains) | 0.23 |
| Gelatin | 1.34 |
| Cyan coupler (see Table 6) | 3.0 × 10⁻⁴ mol/m² |
| Image-dye stabilizer (Cpd-6) | 0.17 |
| Image-dye stabilizer (Cpd-7) | 0.40 |
| Image-dye stabilizer (Cpd-8) | 0.04 |
| Solvent (Solv-6) | 0.15 |
| Sixth layer (Ultraviolet ray absorbing layer): | |
| Gelatin | 0.53 |
| Ultraviolet absorber (UV-1) | 0.16 |
| Color-mix inhibitor (Cpd-5) | 0.02 |
| Solvent (Solv-5) | 0.08 |
| Seventh layer (Protective layer): | |
| Gelatin | 1.33 |
| Acryl-modified copolymer of polyvinyl alcohol (modification degree: 17%) | 0.17 |
| Liquid paraffin | 0.03 |

Compounds used are as follows:

(ExY) Yellow coupler
Mixture (1:1 in molar ratio) of

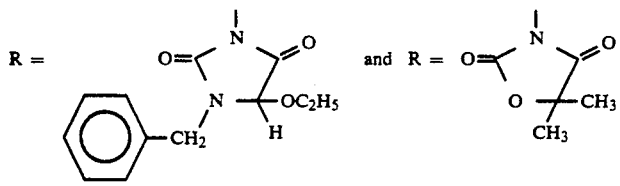

of the following formula

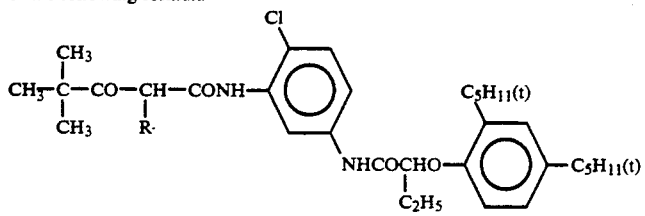

(ExM) Magenta coupler
Mixture (1:1 in molar ratio) of

-continued
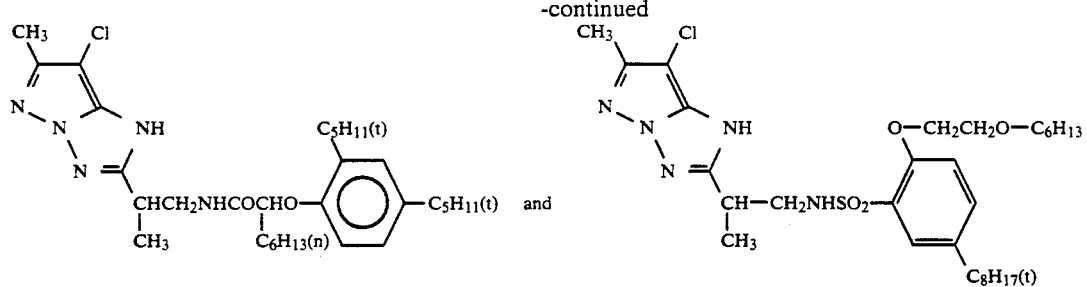
(Cpd-1) Image-dye stabilizer
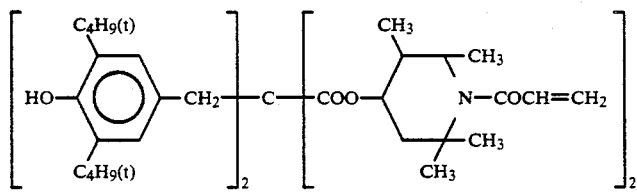
(Cpd-2) Image-dye stabilizer    (Cpd-3) Image-dye stabilizer
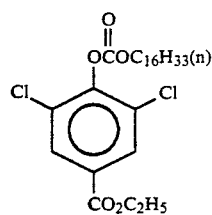
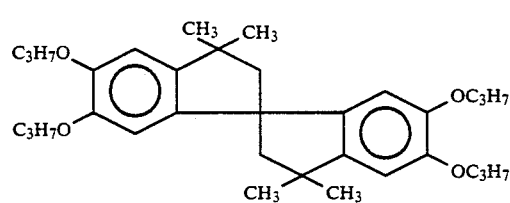
(Cpd-4) Image-dye stabilizer
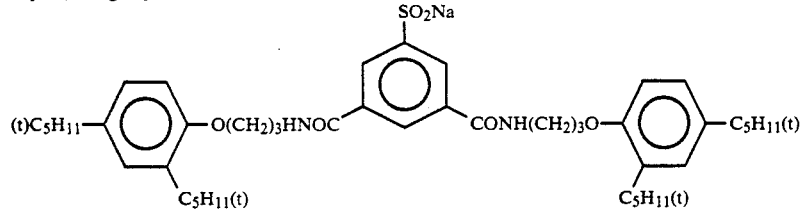
(Cpd-5) Color-mix inhibitor
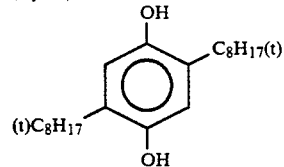
(Cpd-6) Image-dye stabilizer
Mixture (2:4:4 in weight ratio) of
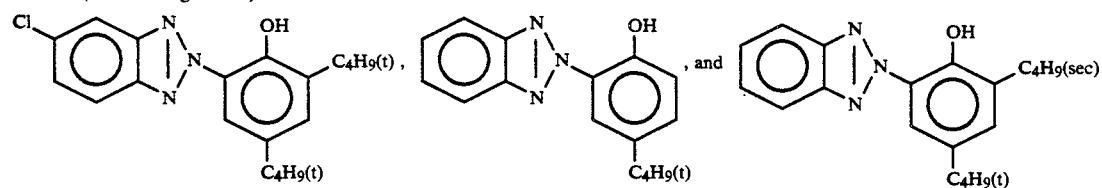
(Cpd-7) Image-dye stabilizer    (Cpd-8) Image-dye stabilizer    (Cpd-9) Image-dye stabilizer
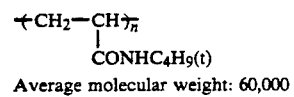
Average molecular weight: 60,000
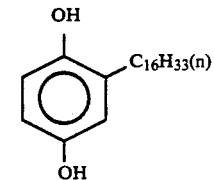
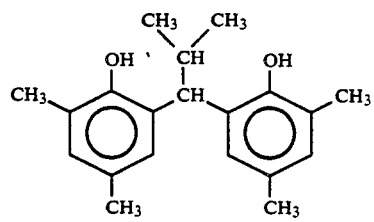

-continued (UV-1) Ultraviolet ray absorber
Mixture (4:2:4 in weight ratio) of

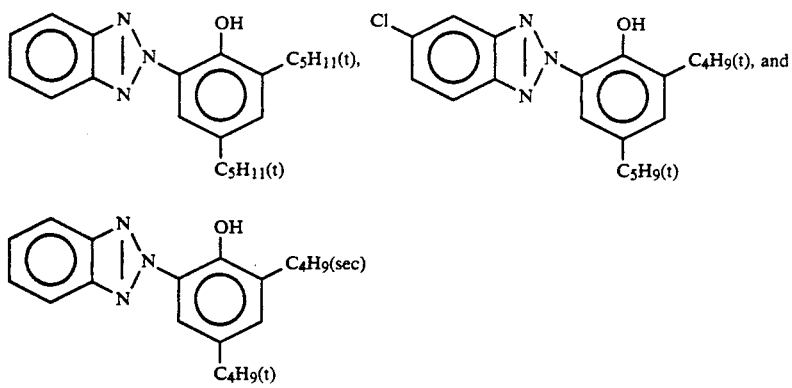

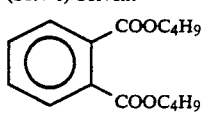
(Solv-1) Solvent (Solv-2) Solvent
Mixture (2:1 in volume ratio) of

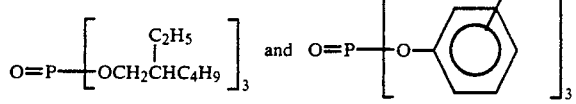
and (Solv-4) Solvent 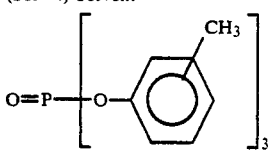

(Solv-5) Solvent 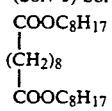

(Solv-6) Solvent 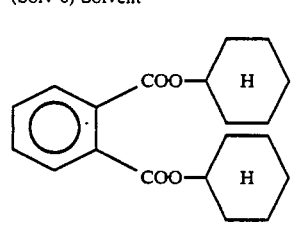

Each of photographic materials above described was subjected to an exposure to red light through an wedge having continuous densities.

After exposure to light, each sample was subjected to a continuous processing (running test) by the processing process shown below using a paper-processor, until a volume of color developer twice that of a tank had been replenished.

| Processing step | Temperature | Time | Replenisher* | Tank Volume |
|---|---|---|---|---|
| Color developing | 35° C. | | 161 ml | 17 l |
| Bleach-fixing | 30–35° C. | 45 sec. | 215 ml | 17 l |
| Rinsing ① | 30–35° C. | 20 sec. | — | 10 l |
| Rinsing ② | 30–35° C. | 20 sec. | — | 10 l |
| Rinsing ③ | 30–35° C. | 20 sec. | 350 ml | 10 l |
| Drying | 70–80° C. | 60 sec. | | |

Note:
*Replenisher amount: ml per m² of photographic material.
Rinsing steps were carried out in three tanks counter-current flow system from the tank of rinsing ③ towards the tank of rinsing ①.

The compositions of each processing solution were as follows:

| Color developer | Tank Solution | Replenisher |
|---|---|---|
| Water | 800 ml | 800 ml |
| Ethylenediamine-N,N,N',N'-tetramethylenephosphonic acid | 1.5 g | 2.0 g |
| Triethanolamine | 8.0 g | 12.0 g |
| Sodium chloride | 1.4 g | — |
| Potassium carbonate | 25 g | 25 g |
| N-Ethyl-N-(β-methanesulfonamidoethyl)-3-methyl-4-aminoaniline sulfonate | 5.0 g | 7.0 g |
| N,N-Bis(carboxymethyl)hydrazine | 5.5 g | 7.0 g |
| Fluorescent brightening agent (WHITEX-4B, made by Sumitomo Chemical Ind. Co.) | 1.0 g | 2.0 g |
| Water to make | 1000 ml | 1000 ml |
| pH (25° C.) | 10.05 | 10.45 |

| Bleach-fixing solution (Both tank solution and replenisher) | |
|---|---|
| Water | 400 ml |
| Ammonium thiosulfate (70%) | 100 ml |
| Sodium sulfite | 17 g |
| Iron (III) ammonium ethylenediaminetetraacetate dihydrate | 55 g |
| Disodium ethylenediaminetetraacetate | 5 g |
| Ammonium bromide | 40 g |
| Water to make | 1000 m |
| pH (25° C.) | 6.0 |

| Rinsing solution (Both tank solution and replenisher) |
|---|
| Ion-exchanged water (Calcium and magnesium each are contained in an amount of 3 ppm or below) |

Maximum densities of red on the samples (601 to 617) colored by processing process are shown in Table 6. (Each figure is a relative value when assumed the maximum red density of Sample 601 being 1.)

TABLE 6

| Sample No. | Coupler | Density |
|---|---|---|
| 601 | A (Comparative) | 1.00 |

TABLE 6-continued

| Sample No. | Coupler | Density |
|---|---|---|
| 602 | B (Comparative) | 0.92 |
| 603 | C (Comparative) | 0.95 |
| 604 | 102 (This Invention) | 1.31 |
| 605 | 103 (This Invention) | 1.25 |
| 606 | 104 (This Invention) | 1.30 |
| 607 | 105 (This Invention) | 1.27 |
| 608 | 106 (This Invention) | 1.25 |
| 609 | 107 (This Invention) | 1.32 |
| 610 | 109 (This Invention) | 1.19 |
| 611 | 113 (This Invention) | 1.22 |
| 612 | 121 (This Invention) | 1.24 |
| 613 | 122 (This Invention) | 1.23 |
| 614 | 123 (This Invention) | 1.31 |
| 615 | 124 (This Invention) | 1.29 |
| 616 | 129 (This Invention) | 1.25 |
| 617 | 131 (This Invention) | 1.26 |

As is apparent from the results of Table 6, it can be noticed that multilayer photographic materials utilizing a reflective base also show high color-forming property.

Having described our invention as related to the embodiment, it is our intention that the invention not be limited by any of the details of the description, unless otherwise specified, but rather be construed broadly within its spirit and scope as set out in the accompanying claims.

What we claim is:

1. A silver halide color photographic material having at least one silver halide emulsion layer on a base, which comprises at least one cyan dye-forming coupler represented by the following formula (I):

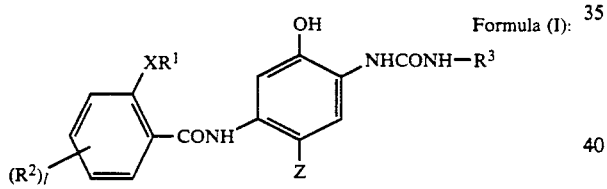

Formula (I)

wherein:

$R^1$ represents an alkyl group, an alkenyl group, a cycloalkyl group, or an aryl group, $R^2$ represents a group capable of substitution onto a benzene ring, $R^3$ is a phenyl group selected from the group consisting of 4-cyanophenyl, 4-cyano-3-halogenophenyl, 3-cyano-4-halogenophenyl, 4-alkylsulfonylphenyl, 4-alkylsulfonyl-3-halogenophenyl, 4-alkylsulfonyl-3-alkoxyphenyl, 3-alkoxy-4-alkylsulfonylphenyl, 3,4-dihalogenophenyl, 4-halogenophenyl, 3,4,5-trihalogenophenyl, 3,4-dicyanophenyl, 3-cyano-4,5-dihalogenophenyl, 4-trifluoromethylphenyl and 3-sulfonamidophenyl X represents —O— or —$SO_2$—, Z represents a hydrogen atom or a group capable of being released upon coupling, and l is an integer of 0 to 4.

2. The silver halide color photographic material as claimed in claim 1, wherein $R^1$ in formula (I) is a straight-chain, branched-chain, or substituted alkyl group.

3. The silver halide color photographic material as claimed in claim 1, wherein $R^3$ in formula (I) is a phenyl group selected from the group consisting of 4-cyanophenyl, 3-cyano-4-halogenophenyl, 3,4-dicyanophenyl and 4-alkylsulfonylphenyl.

4. The silver halide color photographic material as claimed in claim 1, wherein $R^2$ is formula (I) is selected from the group consisting of a halogen atom, a hydroxyl group, a carboxyl group, a sulfo group, a cyano group, a nitro group, an amino group, an alkyl group, an alkenyl group, an alkynyl group, a cycloalkyl group, an aryl group, an alkoxy group, an aryloxy group, an alkylthio group, an alkylsulfonyl group, an arylsulfonyl group, an acyl group, an acyloxy group, an alkoxycarbonyl group, an aryloxycarbonyl group, a carbonamido group, a sulfonamido group, a carbamoyl group, a sulfamoyl group, a ureido group, an alkoxycarbonylamino group, a sulfamoylamino group, an alkoxysulfonyl group, an imido group, and a heterocyclic group.

5. The silver halide color photographic material as claimed in claim 1, wherein Z in formula (I) is selected from the group consisting of a halogen atom, a chlorine atom, a group represented by formula (II) given below, and a group represented by formula (III) given below:

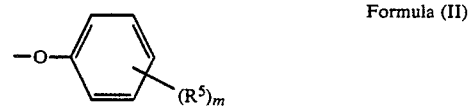

Formula (II)

wherein $R^5$ represents a halogen atom, a cyano group, a nitro group, an alkyl group, an alkoxy group, an alkylthio group, an alkylsulfonyl group, an arylsulfonyl group, a carbonamido group, a sulfonamido group, an alkoxycarbonyl group, a carbamoyl group, a sulfamoyl group, or a carboxyl group, m is an integer of 0 to 5,

Formula (III)

wherein W represents an oxygen atom or a sulfur atom, $R^6$ and $R^7$ each represent a hydrogen atom or a monovalent group, Y represents

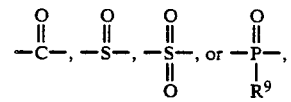

$R^8$ and $R^9$ each represent a hydroxyl group, an alkyl group, an aryl group, an alkoxy group, an alkenyloxy group, an aryloxy group, or a substituted or unsubstituted amino group, n is an integer of 1 to 6.

6. The silver halide color photographic material as claimed in claim 1, wherein X in formula (I) represents —O—.

7. The silver halide color photographic material as claimed in claim 1, wherein X in formula (I) represents —$SO_2$.

8. The silver halide color photographic material as claimed in claim 1, wherein the cyan coupler represented by formula (I) is used in an amount of 0.002 to 2 mol per mol of the photosensitive silver halide.

9. The silver halide color photographic material as claimed in claim 1, wherein the coating amount of the cyan coupler represented by formula (I) is 0.01 to 5 millimol per square meter of the photographic material.

10. The silver halide color photographic material as claimed in claim 1, wherein the cyan coupler represented by formula (I) is introduced into the photographic material by an oil-in-water dispersion process using a high-boiling organic solvent in a weight ratio of 2.0 to 0 to the coupler.

11. The silver halide color photographic material as claimed in claim 11, wherein the high-boiling organic solvent is selected from phthalates.

12. The silver halide color photographic material as claimed in claim 1, wherein the cyan coupler represented by formula (I) is in a photosensitive emulsion layer.

13. The silver halide color photographic material as claimed in claim 1, wherein the cyan coupler represented by formula (I) is in a red-sensitive emulsion layer.

14. The silver halide color photographic material as claimed in claim 1, wherein the silver halide emulsion is a high-silver-chloride emulsion the content of silver chloride of which is 90 mol % or over.

15. The silver halide color photographic material as claimed in claim 1, wherein $R^1$ in formula (I) is a straight-chain or branched chain alkyl group having 1–36 carbon atoms, a straight-chain or branched-chain alkenyl group having 2 to 36 carbon atoms, a 3 to 12-membered cycloalkyl group having 3 to 36 carbon atoms, or an aryl group having 3 to 36 carbon atoms.

16. The silver halide color photographic material as claimed in claim 1, wherein $R^2$ in formula (I) is a halogen atom, an alkyl group having 1 to 24 carbon atoms, a cycloalkyl group having 3 to 24 carbon atoms, an alkoxy group having 1 to 24 carbon atoms, a carbonamido group having 2 to 24 carbon atoms, or a sulfonamido group having 1 to 24 carbon atoms.

17. The silver halide color photographic material as claimed in claim 1, wherein l is an integer of 0 to 2.

* * * * *